(12) United States Patent
Dietrich et al.

(10) Patent No.: US 8,283,495 B2
(45) Date of Patent: Oct. 9, 2012

(54) PROCESS FOR PREPARING OPTICALLY ACTIVE CYCLIC AMINES

(75) Inventors: Hansjörg Dietrich, Hofheim (DE); Mark James Ford, Schmitten-Oberreifenberg (DE); Thomas Müller, Offenbach (DE); José Maria Lassaletta Simon, Seville (ES); Abel Ros Laó, Seville (ES); Antonio Magriz Tascón, Lebrija (ES)

(73) Assignee: Bayer Cropscience GmbH, Frankfurt (DE)

( * ) Notice: Subject to any disclaimer, the term of this patent is extended or adjusted under 35 U.S.C. 154(b) by 1506 days.

(21) Appl. No.: 11/320,121

(22) Filed: Dec. 28, 2005

(65) Prior Publication Data

US 2006/0149080 A1 Jul. 6, 2006

(30) Foreign Application Priority Data

Dec. 30, 2004 (DE) .......... 10 2004 063 443

(51) Int. Cl.
C07C 211/42 (2006.01)
(52) U.S. Cl. ..................... 564/428
(58) Field of Classification Search .......... 564/428
See application file for complete search history.

(56) References Cited

U.S. PATENT DOCUMENTS 5,011,995 A * 4/1991 Pugin et al. ............... 564/302

FOREIGN PATENT DOCUMENTS

EP 0 916 637 A1 5/1999
WO WO 2004/069814 8/2004

OTHER PUBLICATIONS

Ros et al. "Transfer Hydrogenation of a-Branched Ketimines: Enantioselective Synthesis of cycloalkylamines via Dynamic Kinetic Resolution" Advanced Synthesis & Catalysis, 2005, vol. 347, Iss 15, pp. 1917-1920.*
Breuer et al; Industrial Methods for the Production of Optically Active Intermediates; Angew Chem. Int. Ed. 2004 , 43, 788-824.
Matsumoto et al, Diastereoselective Synthesis of a Key Intermediate for the Preparation of Tricyclic β-Lactam Antibiotics; Tetrahedron Letters 40 (1999) 5043-5046.
Murata et al, A Practical Stereoselective Synthesis of Chiral Hydrobenzoins Via Asymmetric Transfer Hydrogenation of Benzils, Organic Letters, 1999, vol. 1, No. 7, 1119-1121.
Ohkuma et al, Stereoselective Hydrogenation of Simple Ketones Catalyzed by Ruthenium (II) Complexes, J. Org. Chem. 1996, 61, 4872-4873.
Helene Pellissier, Dynamic Kinetic Resolution, Tetrahedron 59 (2003) 8291-8327.
Robison et al; Kinetic Resolution Strategies Using Non-Enzymatic Catalysts, Tetrahedron: Asymmetry 14 (2003) 1407-1446.
Angew Chem. Int. Ed. vol. 40, (20011) pp. 40-73.
Nachtsheim et al, Die asymmetrische Synthese von cis-1 R,2R- und cis-1 S,2S-2-Arylcyclohexanaminen, Eingegangen am, Apr. 11, 1998, pp. 187-197.
Massey et al; "Optically Active Amines. VI. Terpenes. The stereochemistry and absolute configurations of the thujylamines and some related compounds" Journal of Organic Chemistry, 31 (3) , XP002366802, 1966.
Wiehl et al, "Synthese und Absolute Konfiguration 2-substituierter Cyclopentanamine", Chem. Ber. 119 2668-2667 (1986).
Eguchi et al; Rational De Novo Design of NADH Mimic for Stereoselective Reduction based on Molecular Orbital Calculation; Tetrahedron 54 (1998) 705-714.
Noyori et al, "Asymmetric Catalysis by Architectural and Functional Molecular Engineering: Practical Chemo and Stereoselective Hydrogenation of Keytones",Bd. 40, Nr. 1, Jan. 2001, pp. 41-73, XP000998801 (already of record).

* cited by examiner

*Primary Examiner* — Joseph Kosack
(74) *Attorney, Agent, or Firm* — Frommer Lawrence & Haug LLP

(57) ABSTRACT

Optically active cyclic amines of the formula (I) or salts thereof

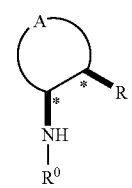

(I)

in which A, $R^0$, R are each as defined in claim 1, and $R^0$ and A, or R and A, or $R^0$ and R may also form rings,
where R and the NH—$R^0$ group on the two ring carbon atoms marked with an asterisk (*) in each case are arranged in cis arrangement to one another and the stereochemical configuration on these carbon atoms is different from the racemic configuration, can be prepared effectively by a process, which comprises converting an imine (a racemic imine) of the formula (II)

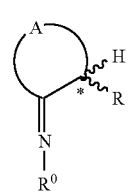

(II)

in which A, $R^0$ and R are each as defined in formula (I), in the presence of hydrogen or a hydrogen donor and a non-enzymatic catalyst which comprises a catalytically active optically active complex of one or more transition metals from the group of ruthenium, rhodium, palladium, iridium, osmium, platinum, iron, nickel and samarium with organic ligands, to the compound of the formula (I).

10 Claims, No Drawings

PROCESS FOR PREPARING OPTICALLY ACTIVE CYCLIC AMINES

The invention relates to the technical field of processes for preparing optically active intermediates which can be used for syntheses of active ingredients, for example active ingredients for crop protection compositions or medicaments.

Optically active compounds are frequently required as intermediates for the preparation of optically active active ingredients. This is true of enantioselective preparation processes in which the desired spatial structure is introduced at certain chiral centers at the stage of an intermediate and is retained up to the active ingredient through one or more process steps. Suitable intermediates are optically active natural substances or compounds in which a chiral center is obtained from achiral compounds with the aid of enantioselective reactions, or racemic compounds for which, in a selective manner, only one of the enantiomers present is converted enantioselectively and used further.

Amino compounds have great significance as intermediates for active crop protection ingredients and active medicament ingredients. Numerous processes for preparing optically active amines are known; see, for example, Angew. Chem. Int. Ed. 2004 (116) 806-843 and literature cited there. In addition to classical optical resolution via diastereomeric salts with optically active acids, some relate to the use of optically active starting materials and enantioselective conversions up to the desired compound. Other processes are based on enzymatic reactions, for example transaminations using enzymes or microorganisms. Other processes again utilize the use of synthetic optically active reagents and their properties in reactions to obtain chiral centers enantioselectively.

The known processes usually have the disadvantage that they can be employed only very specifically on certain substrates. With structurally different substrates, the results with regard to parameters such as chemical yield, enantiomeric excess, selectivity, purity, reaction time and availability of starting materials and auxiliaries are often unsatisfactory. There is therefore a need, in the specific case and also generally, for the provision of alternative processes for preparing optically active amines.

It has now been found that certain optically active cyclic amines with a second, adjacent chiral center can be prepared in a particularly effective manner enantioselectively from compounds which are present in racemic form with regard to the adjacent chiral center.

The invention provides a process for preparing optically active cyclic amines of the formula (I) and salts thereof

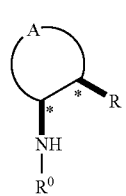

(I)

in which

A, together with the carbon atoms designated with an asterisk (*) in each case, is a carbocyclic or heterocyclic, saturated or unsaturated, nonaromatic ring which has from 3 to 30 ring atoms, preferably from 4 to 9 ring atoms, in particular from 5 to 7 ring atoms, and may be further substituted in addition to the R and NH—$R^0$ radicals, $R^0$, independently of R, is a $(C_1-C_6)$alkyl, $(C_2-C_6)$alkenyl or $(C_3-C_6)$alkynyl radical, where each of the three latter radicals may be unsubstituted or substituted by one or more radicals selected from the group consisting of halogen, cyano, $(C_1-C_6)$alkoxy, $(C_1-C_6)$haloalkoxy, $(C_1-C_6)$alkylthio, $(C_1-C_6)$alkanoyloxy, $(C_1-C_6)$haloalkanoyloxy, aryl, aryloxy, aroyl, aroyloxy and heterocyclyl, where each of the latter 5 radicals is unsubstituted or substituted, or is $(C_3-C_9)$cycloalkyl, $(C_4-C_9)$cycloalkenyl, aryl or heterocyclyl, where each of the latter 4 radicals is unsubstituted or substituted, R, independently of $R^0$, is
  $(C_1-C_6)$alkyl, $(C_2-C_6)$alkenyl or $(C_2-C_6)$alkynyl, where each of the three latter radicals is unsubstituted or substituted by one or more radicals selected from the group consisting of halogen, cyano, $(C_1-C_6)$alkoxy, $(C_1-C_6)$haloalkoxy, $(C_1-C_6)$alkylthio, aryl which is unsubstituted or substituted, and heteroaryl which is unsubstituted or substituted, or
  aryl which is unsubstituted or substituted, or
  heteroaryl which is unsubstituted or substituted, or
$R^0$ and A form a ring B1 and, together with the NH group and the carbon atom which is designated with an asterisk (*) and is bonded to the NH group, are a heterocyclic ring which has from 4 to 30 ring atoms, preferably from 4 to 9 ring atoms, in particular from 5 to 7 ring atoms, and is optionally additionally further substituted and which optionally contains 1 or 2 further heteroatoms from the group of N, O and S, or
R and A form a ring B2 and, together with the carbon atom which is designated with an asterisk (*) and is bonded to R, are a carbocyclic or heterocyclic ring which has from 3 to 30 ring atoms, preferably from 4 to 9 ring atoms, in particular from 5 to 7 ring atoms, and is optionally additionally further substituted, and which, in the case of a heterocyclic ring, contains 1, 2 or 3 heteroatoms from the group of N, O and S, or
$R^0$ and R form a ring B3 and, together with the NH group and the carbon atoms designated with an asterisk (*) in each case, are a heterocyclic ring which has from 4 to 30 ring atoms, preferably from 4 to 9 ring atoms, in particular from 5 to 7 ring atoms, and is optionally additionally further substituted and which optionally contains 1 or 2 further heteroatoms from the group of N, O and S, or
$R^0$ and R and, if appropriate, A may simultaneously form two or more of the rings B1, B2 and B3 mentioned,
where R and the NH—$R^0$ group on the two ring carbon atoms marked with an asterisk (*) in each case are arranged in cis arrangement to one another and the stereochemical configuration on these carbon atoms is different from the racemic configuration,
which comprises converting an imine of the formula (II) or a salt thereof

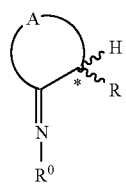

(II)

where A, $R^0$ and R are each as defined in formula (I) and the compound of the formula (II), with regard to the ring carbon atom marked with an asterisk (*), is present in the form of a racemic mixture or in the form of a mixture with any other isomeric ratio of the stereoisomers in question, in the presence of hydrogen or a hydrogen donor and a non-enzymatic catalyst which comprises a catalytically active optically active complex of one or more transition metals from the group of ruthenium, rhodium, palladium, iridium, osmium, platinum, iron, nickel and samarium, preferably one or more transition metals from the group of ruthenium, rhodium, palladium and iridium, especially ruthenium and iridium, with organic ligands, to the compound of the formula (I) or its salt.

The absolute configuration of the product depends in the individual case upon the structure of the optically active catalyst from the group of catalysts mentioned.

Compounds of the formula (I) are especially the compounds of the formulae (I-A) and (I-B)

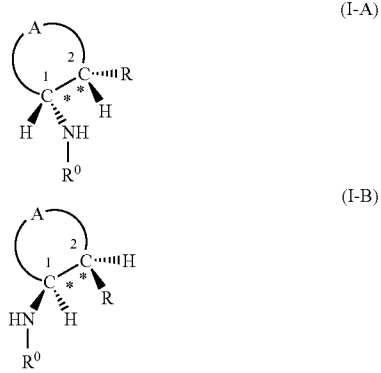

in which A, $R^0$ and R are each as defined above. According to the Cahn-Ingold-Prelog stereochemical nomenclature, the compound (I-A) has, according to the sequence of the substituents on the carbon atom 1, the stereochemical designation (1S-cis) or (1R-cis). The compound (I-B) correspondingly has the stereochemical designation (1R-cis) or (1S-cis).

The compounds (I) with cis configuration on the two chiral centers designated with an asterisk (*) in each case are preferably obtained with a selectivity of from 60 to 100%, preferably from 80 to 100%, in particular from 90 to 100%, very particularly from 95 to 100% in comparison to the trans configuration, the particular cis compound (I-A) or (I-B) being obtained with an enantioselectivity of in each case more than 20% ee or better more than 50% ee, preferably from 60 to 100% ee, in particular from 80 to 100% ee, very particularly from 90 to 100% ee, most preferably from 95 to 100% ee, based on the total content of cis compounds (I-A) and (I-B) in question.

The enantiomeric excess measured in % ee means the difference of the percentages of the two enantiomers based on the mixture of the enantiomers.

The particular compound of the formula (II) consists generally of a mixture of the compounds (II-A1), (II-A2), (II-B1) and (II-B2)

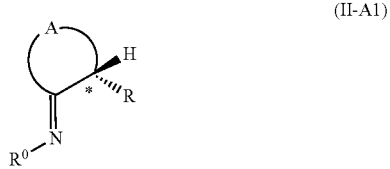

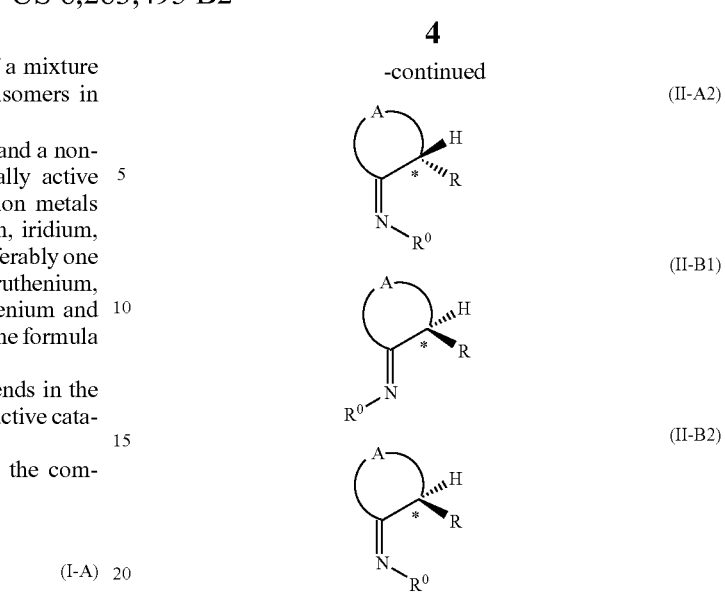

the compounds (II-A1) and (II-A2) being designated together for short as compounds (II-A), and the compounds (II-B1) and (II-B2) being designated together for short as compounds (II-B). The compounds (II-A) and (II-B) may be used generally in any ratio with regard to the configuration on the carbon atom 2. In general, they are present in this regard preferably in the ratio of 1:1, i.e. in a racemic mixture.

The compounds (II-A1) and (II-A2) or (II-B1) and (II-B2) are usually present in equilibrium under the reaction conditions.

When the compounds (I) or (II) can form tautomers by shifting of hydrogen, which would structurally not be covered by the formula (I) or (II) in a formal sense, these tautomers are equally encompassed by the definition of the inventive compounds of the formula (I) or (II).

The compounds of the general formula (I) (or, correspondingly, other inventive compounds) may, depending on the type and attachment of the substituents, contain further chiral centers than the carbon atoms marked with an asterisk (*) in formula (I) and are correspondingly present in the form of stereoisomers. The possible stereoisomers defined by their specific three-dimensional form, such as enantiomers, diastereomers, Z and E isomers, are all encompassed by the formula (I). When, for example, one or more alkenyl groups are present, diastereomers (Z and E isomers) can occur. When, for example, one or more asymmetric carbon atoms are present, enantiomers and diastereomers can occur. Stereoisomers can be obtained from the mixtures obtained in the preparation by customary separation methods, for example by chromatographic separation processes. It is likewise possible to selectively prepare stereoisomers by use of stereoselective reactions using optically active starting materials and/or assistants. The invention thus also relates to all stereoisomers which are encompassed by the general formula (I) but are not specified with their specific stereochemical form, and mixtures thereof.

The possible combinations of the different substituents of the general formula (I) are to be understood such that the general principles of constructing chemical compounds are to be observed, i.e. the formula (I) does not encompass compounds which are known by the skilled worker to be chemically impossible.

The compounds of the formula (I) can form salts, for example by addition of a suitable inorganic or organic acid, for example mineral acids, for example HCl, HBr, $H_2SO_4$ or $HNO_3$, or organic acids such as formic acid, acetic acid, propionic acid, oxalic acid or sulfonic acids, to a basic group, for example the amino group present or other amino groups, alkylamino, dialkylamino, piperidino, morpholino or pyridino. These salts then contain the conjugate base of the acid as an ion.

Salts can be formed by the action of a base on those compounds of the formula (I) which bear an acidic hydrogen atom. Suitable bases are, for example, organic amines, and also the hydroxides, carbonates and hydrogencarbonates of ammonium, alkali metals or alkaline earth metals, especially the hydroxide, carbonate and hydrogencarbonate of sodium and potassium. These salts are compounds in which the acidic hydrogen is replaced by a cation, for example metal salts, especially alkali metal salts or alkaline earth metal salts, especially sodium and potassium salts, or else ammonium salts, salts with organic amines or quaternary ammonium salts.

Suitable substituents which are present in deprotonated form, for example sulfonic acids or carboxylic acids, may form internal salts with groups which are themselves protonatable, such as amido groups.

The compounds of the formula (I) and their salts are also referred to below for short as "compounds (I) used in accordance with the invention" or inventive "compounds (I)".

The terms above and used below are familiar to those skilled in the art and have in particular the definitions explained below:

An inorganic radical is a radical without carbon atoms, preferably halogen, OH and its inorganic salts in which the H is replaced by a cation, for example alkali metal and alkaline earth metal salts, $NH_2$ and its ammonium salts with (inorganic) acids, for example mineral acids, $N_3$ (azide), $N_2^+A^-$ (diazonium radical where $A^-$ is an anion), NO, NHOH, $NHNH_2$, $NO_2$, S(O)OH (sulfinic acid radical), $S(O)_2OH$ (or else $SO_3H$ for short, sulfonic acid radical), —O—$SO_2H$ (sulfite), —O—$SO_3H$ (sulfate), —$P(O)(OH)_2$ (phosphonic acid radical), —O—$P(OH)_3$ (phosphate radical), and the hydrated or dehydrated forms of the latter 6 acid radicals and also their (inorganic) salts; the term "inorganic radical" also encompasses the hydrogen radical (the hydrogen atom), the latter often already being part of the unsubstituted basic structure of an organic radical in these definitions (example: "unsubstituted phenyl"); the term "inorganic radical" here preferably does not encompass pseudohalogen groups such as CN, SCN, organic metal complexes, carbonate or COOH, which can be assigned more appropriately to the organic radicals owing to the content of carbon atoms.

In contrast to an inorganic radical, an organic radical is a radical with carbon atoms, and this radical may also be bonded via heteroatoms. It is preferably an optionally substituted hydrocarbon radical or an optionally substituted heterocyclic radical. However, it preferably also encompasses acyl radicals, i.e. radicals of organic acids which are formed by removal of an OH group. Acyl radicals also include sulfonic ester groups, phosphonic ester groups, phosphinic ester groups, each with organic alcohol components (and are then derived from polybasic acids), or alkylsulfonyl or alkylsulfinyl which are derived from sulfonic acids or sulfinic acids.

A hydrocarbon radical is an aliphatic, cycloaliphatic or aromatic monocyclic radical or, in the case of an optionally substituted hydrocarbon radical, also a bicyclic or polycyclic organic radical based on the elements carbon and hydrogen, for example encompassing the radicals alkyl, alkenyl, alkynyl, cycloalkyl, cycloalkenyl, aryl, phenyl, naphthyl, indanyl, indenyl, etc; the same applies to the hydrocarbonoxy radicals. Unless defined more specifically, the hydrocarbon and hydrocarbonoxy radicals in the above definitions have preferably from 1 to 20 carbon atoms, more preferably from 1 to 16 carbon atoms, in particular from 1 to 12 carbon atoms.

The hydrocarbon radicals and the more specific alkyl, alkoxy, haloalkyl, haloalkoxy, alkylamino and alkylthio radicals, and also the corresponding unsaturated and/or substituted radicals may each be straight-chain or branched in the carbon skeleton.

The expression "$(C_1-C_4)$alkyl" means a short notation for open-chain alkyl having from one to 4 carbon atoms in accordance with the range specification for carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, for example "$(C_1-C_6)$alkyl", correspondingly also encompass straight-chain or branched alkyl radicals having a larger number of carbon atoms, i.e. in the example also the alkyl radicals with 5 and 6 carbon atoms. Unless stated specifically, preference is given in the case of hydrocarbon radicals such as alkyl, alkenyl and alkynyl radicals, including in combined radicals, to the lower carbon structures, for example with from 1 to 6 carbon atoms, in particular from 1 to 4 carbon atoms, or, in the case of unsaturated groups, having from 2 to 6 carbon atoms, in particular 2-4 carbon atoms. Alkyl radicals, including in the combined definitions such as alkoxy, haloalkyl, etc., are, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals have the definition of the possible unsaturated radicals corresponding to the alkyl radicals; alkenyl is, for example, vinyl, allyl, 1-methyl-2-propenyl, 2-methyl-2-propenyl, 2-butenyl, pentenyl, 2-methylpentenyl or hexenyl, preferably allyl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl. $(C_2-C_6)$ Alkynyl is, for example, ethynyl, propargyl, 1-methyl-2-propynyl, 2-methyl-2-propynyl, 2-butynyl, 2-pentynyl or 2-hexynyl, preferably propargyl, but-2-yn-1-yl, but-3-yn-1-yl or 1-methyl-but-3-yn-1-yl.

Alkylidene, for example including in the form of $(C_1-C_{10})$ alkylidene, is the radical of a straight-chain or branched alkane which is bonded via a double bond, the position of the bonding site not having been specified. In the case of a branched alkane, by its nature, only positions at which two hydrogen atoms can be replaced by the double bond are possible; radicals are, for example, $=CH_2$, $=CH-CH_3$, $=C(CH_3)-CH_3$, $=C(CH_3)-C_2H_5$ or $=C(C_2H_5)-C_2H_5$.

Cycloalkyl is a carbocyclic, saturated ring system having preferably 3-8 carbon atoms, for example cyclopropyl, cyclobutyl, cyclopentyl or cyclohexyl. Substituted cycloalkyl encompasses cyclic systems with substituents, also encompassing substituents with a double bond on the cycloalkyl radical, for example an alkylidene group such as methylidene. Substituted cycloalkyl also encompasses polycyclic aliphatic systems, for example bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, adamantan-1-yl and adamantan-2-yl.

Cycloalkenyl is a carbocyclic, nonaromatic, partially unsaturated ring system having preferably 4-8 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. In the case of substituted cycloalkenyl, the explanations for substituted cycloalkyl apply correspondingly. In particular, substituted cycloalkenyl also encompasses corresponding fused polycyclic compounds, for example benzofused compounds such as tetrahydronaphthalin-1-yl or -2-yl, fluorenyl(biphenylmethyl) or suberyl(di-[b,f]-benzocyclohepta-2,6-dien-1-yl).

The term "halogen" means, for example, fluorine, chlorine, bromine or iodine. Haloalkyl, -alkenyl and -alkynyl mean alkyl, alkenyl and alkynyl substituted partly or fully by identical or different halogen atoms, preferably form the group of fluorine, chlorine and bromine, especially from the group of fluorine and chlorine, for example monohaloalkyl such as $CH_2CH_2Cl$, $CH_2CH_2F$, $CH_2ClCH_3$, $CH_2FCH_3$, $CH_2Cl$, $CH_2F$; perhaloalkyl such as $CCl_3$ or $CF_3$ or $CF_3CF_2$; polyhaloalkyl such as $CHF_2$, $CH_2F$, $CH_2FCHCl$, $CHCl_2$, $CF_2CF_2H$, $CH_2CF_3$, $CH_2ClCH_3$, $CH_2FCH_3$; haloalkoxy is, for example, $OCF_3$, $OCHF_2$, $OCH_2F$, $CF_3CF_2O$, $OCH_2CF_3$ and $OCH_2CH_2Cl$; the same applies to haloalkenyl and other radicals substituted by halogen.

Aryl is a mono-, bi- or polycyclic aromatic system having preferably from 6 to 14, in particular from 6 to 12 carbon atoms, for example phenyl, naphthyl, tetrahydronaphthyl, indenyl, indanyl, pentalenyl, fluorenyl, biphenylyl and the like, preferably phenyl.

A heterocyclic radical or ring (heterocyclyl) contains at least one heterocyclic ring which is saturated, unsaturated or heteroaromatic and which may be fused in the generally substituted case with other carbocyclic or heterocyclic rings; unless defined differently, the heterocyclic ring contains preferably from 3 to 9 ring atoms, in particular from 3 to 6 ring atoms, and one or more, preferably from 1 to 4, in particular 1, 2 or 3 heteroatoms in the heterocyclic ring, preferably from the group of N, O and S, although two oxygen atoms should not be directly adjacent and at least one carbon atom also has to be present in the ring, for example a radical of thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-tetrazine, quinoline, isoquinoline, quinoxaline, quinazoline, quinoline, 1,8-naphthyridine, 1,5-naphthyridine, 1,6-naphthyridine, 1,7-naphthyridine, phthalazine, pyridopyrimidine, purine, pteridine, 4H-quinolizine, piperidine, morpholine, piperazine, oxetane, oxirane, pyrrolidine, oxazoline, tetrahydrofuran, tetrahydropyran, 1,3-dioxolane, 1,3- and 1,4-dioxane, isoxazolidine or thiazolidine.

Among the groups mentioned above under "heterocyclyl", "heteroaryl" in each case means the fully unsaturated aromatic heterocyclic compounds, for example pyridine, pyrimidine, (1,2,4)-oxadiazole, (1,3,4)-oxadiazole, pyrrole, furan, thiophene, oxazole, Thiazole, imidazole, pyrazole, isoxazole, 1,2,4-triazole, tetrazole, pyrazine or pyridazine.

Preference is further given to heterocyclyl being a partially or fully hydrogenated heterocyclic radical having a heteroatom from the group of N, O and S, for example oxiranyl, oxetanyl, oxolanyl(=tetrahydrofuryl), oxanyl, pyrrolinyl, pyrrolidinyl or piperidinyl.

Preference is further given to it being a partially or fully hydrogenated heterocyclic radical having 2 heteroatoms from the group of N, O and S, for example oxazolinyl, thiazolinyl, piperazinyl, 1,3-dioxolanyl, 1,3- and 1,4-dioxanyl, oxazolinyl, isoxazolinyl, oxazolidinyl, isoxazolidinyl and morpholinyl.

When it is a partly or fully saturated nitrogen heterocycle, it may be bonded to the radical of the molecule of the particular compound either via carbon or via the nitrogen.

Heterocyclyl is preferably an aliphatic, saturated or unsaturated, especially saturated, heterocyclyl radical having from 3 to 7, in particular from 3 to 6 ring atoms, or a heteroaromatic radical having 5 or 6 ring atoms. Heterocyclyl preferably contains heterocyclic ring atoms from the group of N, O and S.

Preferred examples of heterocyclyl are a heterocyclic radical having from 3 to 6 ring atoms from the group of pyridyl, thienyl, furyl, pyrrolyl, oxiranyl, 2-oxetanyl, 3-oxetanyl, oxolanyl (=tetrahydrofuryl), pyrrolidinyl, piperidinyl, in particular oxiranyl, 2-oxetanyl, 3-oxetanyl or oxolanyl, or a heterocyclic radical having two or three heteroatoms, for example pyrimidinyl, pyridazinyl, pyrazinyl, triazinyl, thienyl, thiazolyl, thiadiazolyl, oxazolyl, isoxazolyl, pyrazolyl, triazolyl, piperazinyl, dioxolanyl, dioxanyl, oxazolinyl, isoxazolinyl, oxazolidinyl, isoxazolidinyl or morpholinyl.

When a basic structure is substituted "by one or more radicals" from a list of radicals (=group) or a generically defined group of radicals, this in each case includes the simultaneous substitution by a plurality of identical and/or structurally different radicals.

In the case of a plurality of optionally substituted basic structures, the definition "where each of the latter radicals (=basic structures) is unsubstituted or substituted" means that each of the radicals (=basic structures) is unsubstituted or substituted independently of the other radicals.

Possible substituents for a substituted heterocyclic radical include the substituents mentioned below, and additionally also oxo. The oxo group as a substituent then means, for example, a carbonyl group in the heterocyclic ring. Thus, lactones and lactams are preferably also encompassed. The oxo group may also occur on the heterocyclic ring atoms which can exist in various oxidation states, for example in the case of N and S, and in that case form, for example, the divalent groups —N(O)—, —S(O)— (also SO for short) and —S(O)$_2$— (also SO$_2$ for short) in the heterocyclic ring.

Substituted radicals such as a substituted alkyl, alkenyl, alkynyl, cycloalkyl, cycloalkenyl, aryl, phenyl, benzyl, heterocyclyl and heteroaryl radical, are, for example, a substituted radical derived from the unsubstituted basic structure, the substituents being, for example, one or more, preferably 1, 2 or 3 radicals from the group of halogen, alkoxy, alkylthio, hydroxy, amino, nitro, carboxy, cyano, azido, alkoxycarbonyl, alkanoyl, alkoxycarbonyloxy, alkanoyloxy, aryloxycarbonyl, aryloxycarbonyloxy, carbamoyl, mono- and dialkylaminocarbonyl, substituted amino such as acylamino, mono- and dialkylamino, trialkylsilyl and optionally substituted cycloalkyl, optionally substituted aryl, optionally substituted heterocyclyl, where each of the latter cyclic groups may also be bonded via heteroatoms or divalent functional groups as in the case of the alkyl radicals mentioned, and alkylsulfinyl, alkylsulfonyl, and, in the case of cyclic radicals (="cyclic basic structures"), also alkyl, haloalkyl, alkylthioalkyl, alkoxyalkyl, optionally substituted mono- and dialkylaminoalkyl and hydroxyalkyl; in the term "substituted radicals" such as substituted alkyl, etc., included as substituents in addition to the saturated hydrocarbon-containing radicals mentioned are corresponding unsaturated aliphatic and aromatic radicals such as optionally substituted alkenyl, alkynyl, alkenyloxy, alkynyloxy, phenyl, phenoxy, etc.

Substituted cyclic radicals with aliphatic moieties in the ring also encompass cyclic systems with such substituents which are bonded to the ring with a double bond, for example with an alkylidene group such as methylidene or ethylidene, or an oxo group, imino group or substituted imino group.

The substituents mentioned by way of example ("first substituent level") may, when they contain hydrocarbon-containing moieties, optionally further be substituted there ("second substituent level"), for example by one of the substituents as defined for the first substituent level. Corresponding further substituent levels are possible. The term "substituted radical" preferably encompasses only one or two substituent levels.

Preferred substituents for the substituent levels are, for example, amino, hydroxy, halogen, nitro, cyano, mercapto, carboxy, carbonamide, $SF_5$, aminosulfonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, arylcarbonyloxy, alkanoyloxy, alkenylcarbonyloxy, alkynylcarbonyloxy, alkoxycarbonyloxy, alkenyloxycarbonyloxy, alkynyloxycarbonyloxy, aryloxycarbonyloxy, alkylthio, cycloalkylthio, alkenylthio, cycloalkenylthio, alkynylthio, alkylsulfinyl, alkylsulfonyl, monoalkylaminosulfonyl, dialkylaminosulfonyl, N-alkylaminocarbonyl, N,N-dialkylaminocarbonyl, N-alkanoylaminocarbonyl, N-alkanoyl-N-alkyl-aminocarbonyl, aryl, aryloxy, benzyl, benzyloxy, benzylthio, arylthio, arylamino, benzylamino, heterocyclyl and trialkylsilyl.

In the case of radicals with carbon atoms, preference is given to those having from 1 to 6 carbon atoms, preferably from 1 to 4 carbon atoms, in particular 1 or 2 carbon atoms. Preference is generally given to substituents from the group of halogen, e.g. fluorine or chlorine $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Particular preference is given to the substituents methyl, methoxy, fluorine and chlorine.

Substituted amino such as mono- or disubstituted amino is a radical from the group of the substituted amino radicals which is n-substituted, for example, by one or two identical or different radicals from the group of alkyl, alkoxy, acyl and aryl; preferably mono- and dialkylamino, mono- and diarylamino, acylamino, N-alkyl-N-arylamino, N-alkyl-N-acylamino, and also saturated H-heterocycles; preference is given to alkyl radicals having from 1 to 4 carbon atoms; aryl is preferably phenyl or substituted phenyl; for acyl, the definition specified below applies, preferably $(C_1-C_4)$alkanoyl. The same applies to substituted hydroxylamino or hydrazino.

Optionally substituted phenyl is preferably phenyl which is unsubstituted or mono- or polysubstituted, preferably up to trisubstituted, by identical or different radicals from the group of halogen, $(C_1-C_4)$alkyl, $(C_1-C_4)$alkoxy, $(C_1-C_4)$haloalkyl, $(C_1-C_4)$haloalkoxy and nitro, for example o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxyphenyl.

Optionally substituted cycloalkyl is preferably cycloalkyl which is unsubstituted or mono- or polysubstituted, preferably up to trisubstituted, by identical or different radicals from the group of halogen, $(C_1-C_4)$alkyl, $(C_1-C_4)$alkoxy, $(C_1-C_4)$haloalkyl and $(C_1-C_4)$haloalkoxy, especially by one or two $(C_1-C_4)$alkyl radicals.

Optionally substituted heterocyclyl is preferably heterocyclyl which is unsubstituted or mono- or polysubstituted, preferably up to trisubstituted, by identical or different radicals from the group of halogen, $(C_1-C_4)$alkyl, $(C_1-C_4)$alkoxy, $(C_1-C_4)$haloalkyl, $(C_1-C_4)$haloalkoxy, nitro and oxo, especially mono- or polysubstituted by radicals from the group of halogen, $(C_1-C_4)$alkyl, $(C_1-C_4)$alkoxy, $(C_1-C_4)$haloalkyl and oxo, very particularly by one or two $(C_1-C_4)$alkyl radicals.

Acyl is a radical of an organic acid which is formed, in a formal sense, by removing a hydroxyl group at the acid function, and the organic radical in the acid may also be bonded with the acid function via a heteroatom. Examples of acyl are the —CO—R radical of a carboxylic acid HO—CO—R and radicals of acids derived therefrom, such as of thiocarboxylic acid, optionally N-substituted iminocarboxylic acids, or the radical of carbonic monoesters, N-substituted carbamic acid, sulfonic acids, sulfinic acids, N-substituted sulfonamide acids, phosphonic acids, phosphinic acids.

Acyl is, for example, alkanoyl such as formyl or [$(C_1-C_4)$alkyl]carbonyl, phenylcarbonyl, alkyloxycarbonyl, phenyloxycarbonyl, benzyloxycarbonyl, alkylsulfonyl, alkylsulfinyl, N-alkyl-1-iminoalkyl, N-alkyl- and N,N-dialkylcarbamoyl and other radicals of organic acids. The radicals may each be further substituted in the alkyl or phenyl moiety, for example in the alkyl moiety by one or more radicals from the group of halogen, alkoxy, phenyl and phenoxy; examples of substituents in the phenyl moiety are the substituents already mentioned above in general for substituted phenyl.

Acyl is preferably an acyl radical in the narrower sense, i.e. a radical of an organic acid in which the acid group is bonded directly to the carbon atom of an organic radical, for example alkanoyl such as formyl and acetyl, aroyl such as phenylcarbonyl, and other radicals of saturated or unsaturated organic acids.

"Aroyl" is an aryl radical as defined above which is bonded via a carbonyl group, for example the benzoyl group.

When a general radical is defined as hydrogen, this means a hydrogen atom.

"yl position" of a radical designates its binding site.

For reasons of better preparability, especially with regard to yield, space-time yield, enantioselectivity of the process and simplicity of the process, but also for reasons of usability, closer interest attaches to inventive processes for preparing amino compounds of the formula (I) in which A, together with the carbon atoms designated with an asterisk (*) in each case, is a carbocyclic or heterocyclic, saturated or unsaturated, nonaromatic ring which has from 4 to 9 ring atoms, in particular from 5 to 7 ring atoms, and, in addition to the R and NH—$R^0$ radicals, is unsubstituted or further substituted by one or more radicals selected from the group consisting of halogen, hydroxy, amino, cyano, nitro, $(C_1-C_4)$alkyl, $(C_3-C_9)$cycloalkyl, $(C_2-C_4)$alkenyl, $(C_5-C_9)$cycloalkenyl, $(C_2-C_4)$alkynyl, $(C_1-C_4)$alkoxy, $(C_1-C_4)$alkoxycarbonyl, $(C_1-C_4)$alkylthio, $(C_1-C_4)$alkylsulfonyl, aryl and heterocyclyl, where the latter 11 radicals are each independently unsubstituted or substituted by one or more radicals selected from the group consisting of halogen, cyano, $(C_3-C_9)$cycloalkyl, $(C_4-C_9)$cycloalkenyl, $(C_1-C_4)$alkoxy, $(C_1-C_4)$alkylthio and, in the case of cyclic radicals, also $(C_1-C_4)$alkyl and $(C_1-C_4)$haloalkyl, and is optionally substituted by a fused carbocyclic or heterocyclic ring which has from 3 to 30 ring atoms and, in the case of a heterocyclic ring, contains from 1 to 3 ring atoms from the group of N, O and S, and is optionally further substituted by one or more radicals selected from the group consisting of halogen, cyano, $(C_1-C_4)$alkyl, $(C_3-C_9)$cycloalkyl, $(C_2-C_4)$alkenyl, $(C_5-C_9)$cycloalkenyl, $(C_2-C_4)$alkynyl, $(C_1-C_4)$alkoxy and $(C_1-C_4)$alkylthio, where each of the latter 7 radicals is independently unsubstituted or substituted by one or more radicals selected from the group consisting of halogen, cyano, $(C_3-C_9)$cycloalkyl, $(C_4-C_9)$cycloalkenyl, ($C_1$-$C_4$)alkoxy, ($C_1$-$C_4$)alkylthio and, in the case of cyclic radicals, also ($C_1$-$C_4$)alkyl and ($C_1$-$C_4$)haloalkyl, $R^0$, independently of R, is a ($C_1$-$C_6$)alkyl, ($C_2$-$C_6$)alkenyl or ($C_3$-$C_6$)alkynyl radical, where each of the three latter radicals is unsubstituted or substituted by one or more radicals selected from the group consisting of halogen, cyano, ($C_1$-$C_4$)alkoxy, ($C_1$-$C_4$)haloalkoxy, ($C_1$-$C_4$)alkylthio, ($C_1$-$C_4$)alkanoyloxy, ($C_1$-$C_4$)haloalkanoyloxy, phenyl which is unsubstituted or substituted and heterocyclyl which is unsubstituted or substituted, or ($C_3$-$C_9$)cycloalkyl which is unsubstituted or substituted, preferably unsubstituted or substituted by one or more radicals selected from the group consisting of halogen, cyano, ($C_1$-$C_4$)alkyl, ($C_1$-$C_4$)haloalkyl, ($C_1$-$C_4$)alkoxy, ($C_1$-$C_4$)haloalkoxy, ($C_1$-$C_4$)alkylthio and phenyl which is unsubstituted or substituted, or ($C_4$-$C_9$)cycloalkenyl which is unsubstituted or substituted, preferably unsubstituted or substituted by one or more radicals selected from the group consisting of halogen, cyano, ($C_1$-$C_4$)alkyl, ($C_1$-$C_4$)haloalkyl, ($C_1$-$C_4$)alkoxy, ($C_1$-$C_4$)haloalkoxy, ($C_1$-$C_4$)alkylthio and phenyl which is unsubstituted or substituted, and is optionally fused, preferably benzofused, at one or more double bonds in the ring with an aromatic ring which does or does not have further substitution, or phenyl which is unsubstituted or substituted, preferably unsubstituted or substituted by one or more radicals selected from the group consisting of halogen, cyano, ($C_1$-$C_4$)alkyl, ($C_1$-$C_4$)haloalkyl, ($C_1$-$C_4$)alkoxy, ($C_1$-$C_4$)haloalkoxy, ($C_1$-$C_4$)alkylthio and phenyl which is unsubstituted or substituted, and is optionally fused, preferably benzofused, at one or more double bonds in the ring with an aromatic ring which does or does not have further substitution, or heterocyclyl which is unsubstituted or substituted, preferably unsubstituted or substituted by one or more radicals selected from the group consisting of halogen, cyano, ($C_1$-$C_4$)alkyl, ($C_1$-$C_4$)haloalkyl, ($C_1$-$C_4$)alkoxy, ($C_1$-$C_4$)haloalkoxy, ($C_1$-$C_4$)alkylthio and phenyl which is unsubstituted or substituted, and is optionally, in the case of an unsaturated or heteroaromatic heterocyclyl, fused, preferably benzofused, at one or more double bonds in the ring which does or does not have further substitution, or $R^0$ is in particular an eliminable radical (cleavable group, leaving group) selected from the group consisting of
i) $CH_2C_6H_5$ (benzyl)
ii) $CH_2CH=CH_2$ (allyl)
iii) $C(CH_3)_3$ (t-butyl)
iv) $C(C_6H_5)_3$ (trityl)
v) $CH_3$ (methyl)
vi) $(CH_2)_3OCOCH_3$ (3-acetoxypropyl)
vii) $CH_2C_6H_3$-2,4-$(OCH_3)_2$ (2,4-dimethoxybenzyl)
viii) $C_6H_3$-2,4-$(NO_2)_2$ (2,4-dinitrophenyl)
ix) $CH_2C_6H_4$-4-$OCH_3$ (4-methoxybenzyl)
x) $CH_2C_6H_4$-2-OH (2-hydroxybenzyl)
xi) $CH(C_6H_5)_2$ (diphenylmethyl)
xii) $CH(C_6H_4$-4-$OCH_3)_2$ (bis-(4-methoxyphenyl)methyl)
xiii) $C(C_6H_5)_2(C_6H_{44}—OCH_3)$ (4-methoxyphenyl)diphenylmethyl)
xiv) 5-Dibenzosuberyl(dibenzo-[b,f]-cyclohepta-2,6-dien-1-yl)
xv) 9-Phenylfluoren-9-yl (1-phenyldiphenylenemethyl),
where each of the phenyl or heterocyclyl radicals mentioned, which is unsubstituted or substituted (i.e. is optionally substituted without specification of the substituents), is preferably unsubstituted or substituted by one or more radicals selected from the group consisting of halogen, cyano, nitro, ($C_1$-$C_4$)alkyl, ($C_2$-$C_4$)alkenyl, ($C_2$-$C_4$)alkynyl, ($C_1$-$C_4$)haloalkyl, ($C_1$-$C_4$)alkoxy-($C_1$-$C_4$)alkyl, ($C_1$-$C_4$)alkoxy($C_1$-$C_4$)haloalkoxy, ($C_1$-$C_4$)alkoxy-($C_1$-$C_4$)alkyloxy, ($C_1$-$C_4$)alkylthio, ($C_1$-$C_4$)alkylsulfinyl, ($C_1$-$C_4$)alkylsulfonyl, ($C_1$-$C_4$)alkanoyl, [($C_1$-$C_4$)alkoxy]carbonyl, ($C_1$-$C_4$)alkylamino and di[($C_1$-$C_4$)alkyl]amino; in particular, each of the phenyl or heterocyclyl radicals mentioned which is unsubstituted or substituted is preferably unsubstituted or substituted by one or more radicals selected from the group consisting of halogen, ($C_1$-$C_4$)alkyl, ($C_1$-$C_4$)alkoxy, ($C_1$-$C_4$)haloalkyl, ($C_1$-$C_4$)haloalkoxy and nitro, R, independently of $R^0$, is
($C_1$-$C_6$)alkyl, ($C_2$-$C_6$)alkenyl or ($C_2$-$C_6$)alkynyl, where each of the three latter radicals is unsubstituted or substituted by one or more radicals selected from the group consisting of halogen, cyano, ($C_1$-$C_4$)alkoxy, ($C_1$-$C_4$)haloalkoxy, ($C_1$-$C_4$)alkylthio, aryl which is optionally substituted and heteroaryl which is optionally substituted, or aryl which is optionally substituted, or heteroaryl which is optionally substituted, where the optionally substituted radicals are each independently preferably unsubstituted or substituted by one or more radicals selected from the group consisting of halogen, hydroxy, amino, cyano, nitro, ($C_1$-$C_4$)alkyl, ($C_3$-$C_9$)cycloalkyl, ($C_2$-$C_4$)alkenyl, ($C_5$-$C_9$)cycloalkenyl, ($C_2$-$C_4$)alkynyl, ($C_1$-$C_4$)alkoxy, ($C_1$-$C_5$)alkanoyl, [($C_1$-$C_4$)alkoxy]carbonyl, ($C_1$-$C_4$)alkylthio, ($C_1$-$C_4$)alkylsulfonyl, ($C_1$-$C_4$)alkylamino, di-($C_1$-$C_4$)alkylamino, aryl and heterocyclyl, where the latter 14 radicals are each independently unsubstituted or substituted by one or more radicals selected from the group consisting of halogen, cyano, ($C_3$-$C_9$)cycloalkyl, ($C_5$-$C_9$)cycloalkenyl, ($C_1$-$C_4$)alkoxy, ($C_1$-$C_4$)alkylthio and, in the case of cyclic radicals, also ($C_1$-$C_4$)alkyl and ($C_1$-$C_4$)haloalkyl, or $R^0$ and A form a ring B1 and, together with the NH group and the carbon atom which is designated with an asterisk (*) and is bonded to the NH group, are a heterocyclic ring having from 4 to 30 ring atoms, preferably having from 4 to 9 ring atoms, in particular having from 5 to 7 ring atoms, which is optionally additionally further substituted and which optionally contains one or more further heteroatoms from the group of N, O and S, and are preferably the heterocyclic ring mentioned which does not have further substitution or is substituted by one or more radicals selected from the group consisting of halogen, hydroxy, amino, cyano, nitro, ($C_1$-$C_4$)alkyl, ($C_1$-$C_4$)haloalkyl, ($C_3$-$C_9$)cycloalkyl, ($C_2$-$C_4$)alkenyl, ($C_5$-$C_9$)cycloalkenyl, ($C_2$-$C_4$)alkynyl, ($C_1$-$C_4$)alkoxy, ($C_1$-$C_4$)haloalkoxy, ($C_1$-$C_4$)alkylthio and ($C_1$-$C_4$)alkylsulfonyl, or R and A form a ring B2 and, together with the carbon atom which is designated with an asterisk (*) and bonded to R, form a carbocyclic or heterocyclic ring which has from 3 to 30 ring atoms, preferably from 3 to 9 ring atoms, in particular from 4 to 7 ring atoms, and may optionally additionally be further substituted and, in the case of a heterocyclic ring, contains 1 or 2 or 3 further heteroatoms selected from the group consisting of N, O and S, and are preferably the carbocyclic or heterocyclic ring mentioned which may not have further substitution or may have further substitution by one or more radicals selected from the group consisting of halogen, hydroxy, amino, cyano, nitro, ($C_1$-$C_4$)alkyl, ($C_1$-$C_4$)haloalkyl, ($C_3$-$C_9$)cycloalkyl, ($C_2$-$C_4$)alkenyl, ($C_5$-$C_9$)cycloalkenyl, ($C_2$-$C_4$)alkynyl, ($C_1$-$C_4$)alkoxy, ($C_1$-$C_4$)haloalkoxy, ($C_1$-$C_4$)alkylthio and ($C_1$-$C_4$)alkylsulfonyl, or $R^0$ and R form a ring B3 and, together with the NH group and the carbon atoms designated with an asterisk (*) in each case, are a heterocyclic ring which has from 4 to 30 ring atoms, preferably from 4 to 9 ring atoms, in particular from 5 to 7 ring atoms, and is optionally additionally further substituted and optionally contains 1 or 2 further heteroatoms from the group of N, O and S, and are preferably the heterocyclic ring mentioned which may not have further substitution or may have further substitution by one or more radicals selected from the group consisting of halogen, hydroxy, amino, cyano, nitro, ($C_1$-$C_4$)alkyl, ($C_1$-$C_4$)haloalkyl, ($C_3$-$C_9$)cycloalkyl, ($C_2$-$C_4$)alkenyl, ($C_5$-$C_9$)cycloalkenyl, ($C_2$-$C_4$)alkynyl, ($C_1$-$C_4$)alkoxy, ($C_1$-$C_4$)haloalkoxy, ($C_1$-$C_4$)alkylthio and ($C_1$-$C_4$)alkylsulfonyl, or $R^0$ and R and, if appropriate, A simultaneously form two or more of the rings B1, B2 and B3 mentioned, where R and the NH—$R^0$ group on the two ring carbon atoms marked with an asterisk (*) in each case are arranged in cis arrangement to one another and the stereochemical configuration on these carbon atoms is different from the racemic configuration.

Preferred inventive processes relate, for example, to the preparation of monocyclic compounds of the formula (Ia)

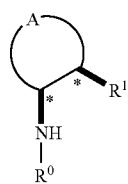

(Ia)

where

A, together with the carbon atoms designated with an asterisk (*) in each case, is a carbocyclic or heterocyclic, saturated or unsaturated, nonaromatic ring having from 3 to 30 ring atoms, preferably having from 4 to 9 ring atoms, in particular having from 5 to 7 ring atoms, and, in the case of a heterocyclic ring which has from 1 to 3 heterocyclic ring atoms selected from the group consisting of N, O and S and, in addition to the $R^1$ and NH—$R^0$ radicals is unsubstituted or further substituted by one or more radicals selected from the group consisting of halogen, hydroxy, amino, cyano, nitro, ($C_1$-$C_4$)alkyl, ($C_3$-$C_9$)cycloalkyl, ($C_1$-$C_4$)alkoxy, ($C_1$-$C_4$)alkoxycarbonyl, ($C_1$-$C_4$)alkylthio, ($C_1$-$C_4$)alkylsulfonyl, aryl and heterocyclyl, where each of the latter 8 radicals is unsubstituted or substituted by one or more radicals selected from the group consisting of halogen, cyano, ($C_3$-$C_9$)cycloalkyl, ($C_1$-$C_4$)alkoxy, ($C_1$-$C_4$)alkylthio and, in the case of cyclic radicals, also ($C_1$-$C_4$)alkyl and ($C_1$-$C_4$)haloalkyl, $R^0$, independently of $R^1$, is as defined above in formula (I), preferably as defined with preference for formula (I) and in particular a ($C_1$-$C_6$)alkyl, ($C_2$-$C_6$)alkenyl or ($C_3$-$C_6$)alkynyl radical, where each of the three latter radicals is unsubstituted or substituted by one or more radicals selected from the group consisting of halogen, cyano, ($C_1$-$C_4$)alkoxy, ($C_1$-$C_4$)haloalkoxy, ($C_1$-$C_4$)alkylthio, ($C_1$-$C_4$)alkanoyloxy, ($C_1$-$C_4$)haloalkanoyloxy and phenyl which is unsubstituted or substituted by one or more radicals selected from the group consisting of halogen, cyano, nitro, ($C_1$-$C_4$)alkyl, ($C_2$-$C_4$)alkenyl, ($C_2$-$C_4$)alkynyl, ($C_1$-$C_4$)haloalkyl, ($C_1$-$C_4$)alkoxy-($C_1$-$C_4$)alkyl, ($C_1$-$C_4$)alkoxy, ($C_1$-$C_4$)haloalkoxy, ($C_1$-$C_4$)alkoxy-($C_1$-$C_4$)alkoxy, ($C_1$-$C_4$)alkylthio, ($C_1$-$C_4$)alkylsulfinyl, ($C_1$-$C_4$)alkylsulfonyl, ($C_1$-$C_4$)-alkanoyl, [($C_1$-$C_4$)alkoxy]carbonyl, ($C_1$-$C_4$)alkylamino and di[($C_1$-$C_4$)alkyl]-amino, and heterocyclyl which is unsubstituted or substituted by one or more radicals selected from the group consisting of halogen, cyano, nitro, ($C_1$-$C_4$)alkyl, ($C_2$-$C_4$)alkenyl, ($C_2$-$C_4$)alkynyl, ($C_1$-$C_4$)haloalkyl, ($C_1$-$C_4$)alkoxy-($C_1$-$C_4$)alkyl, ($C_1$-$C_4$)alkoxy, ($C_1$-$C_4$)haloalkoxy, ($C_1$-$C_4$)alkoxy-($C_1$-$C_4$)alkoxy, ($C_1$-$C_4$)alkylthio, ($C_1$-$C_4$)alkylsulfinyl, ($C_1$-$C_4$)alkylsulfonyl, ($C_1$-$C_4$)-alkanoyl, [($C_1$-$C_4$)alkoxy]carbonyl, ($C_1$-$C_4$)alkylamino and di[($C_1$-$C_4$)alkyl]-amino, or ($C_3$-$C_6$)cycloalkyl, phenyl or heterocyclyl, where each of the 3 latter radicals is optionally substituted, or, for example, one of the abovementioned eliminable radicals i) to xiii), $R^1$, independently of $R^0$, is ($C_1$-$C_6$)alkyl, ($C_2$-$C_6$)alkenyl or ($C_2$-$C_6$)alkynyl, where each of the three latter radicals is unsubstituted or substituted by one or more radicals selected from the group consisting of halogen, cyano, ($C_1$-$C_4$)alkoxy, ($C_1$-$C_4$)haloalkoxy and ($C_1$-$C_4$)alkylthio, or aryl or heterocyclyl, where each of the 2 latter radicals is unsubstituted or substituted, preferably unsubstituted or substituted as in R in formula (I) for optionally substituted phenyl or heterocyclyl, in particular by one or more radicals selected from the group consisting of halogen, ($C_1$-$C_4$)alkyl, ($C_1$-$C_4$)haloalkyl and ($C_1$-$C_4$)haloalkoxy, where the substituents $R^1$ and the amino group on the two ring carbon atoms marked with an asterisk (*) in each case are arranged in cis arrangement to one another and the compound (Ia) is present in the form of a stereochemically pure compound of the formula (Ia-A) or (Ia-B)

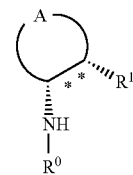

(Ia-A)

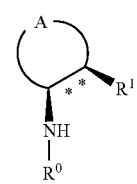

(Ia-B)

in which the general radicals are as defined in formula (Ia), or in the form of an isomer mixture of the compounds of the formulae (Ia-A) and (Ia-B) in an isomer ratio other than the ratio of 1:1.

Preference is also given to processes for preparing bicyclic amino compounds of the formula (Ib)

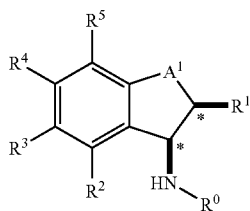

in which

A$^1$ is a direct bond or a group of the formula (CR$^6$R$^7$)$_n$ in which n is from 1 to 6 and R$^6$ and R$^7$ are each independently, or, in the case that n is greater than 1, the R$^6$ and R radicals are in each case independently hydrogen, (C$_1$-C$_4$)alkyl, (C$_1$-C$_4$)haloalkyl, halogen, (C$_1$-C$_4$)alkoxy or (C$_1$-C$_4$)haloalkoxy, where individual CR$^6$R$^7$ groups may be replaced by heteroatoms from the group of O and S, R$^0$ is as defined above in formula (I), preferably as defined with preference for formula (I), and is in particular, independently of R$^1$, a (C$_1$-C$_6$)alkyl or (C$_2$-C$_6$)alkenyl radical, where each of the two latter radicals is unsubstituted or substituted by one or more radicals selected from the group consisting of halogen, cyano, (C$_1$-C$_4$)alkoxy, (C$_1$-C$_4$)haloalkoxy, (C$_1$-C$_4$)alkylthio, (C$_1$-C$_4$)alkanoyloxy, (C$_1$-C$_4$)haloalkanoyloxy and aryl which is unsubstituted or substituted by one or more radicals selected from the group consisting of halogen, cyano, nitro, (C$_1$-C$_4$)alkyl, (C$_2$-C$_4$)alkenyl, (C$_2$-C$_4$)alkynyl, (C$_1$-C$_4$)haloalkyl, (C$_1$-C$_4$)alkoxy-(C$_1$-C$_4$)alkyl, (C$_1$-C$_4$)alkoxy, (C$_1$-C$_4$)haloalkoxy, (C$_1$-C$_4$)alkoxy-(C$_1$-C$_4$)alkoxy, (C$_1$-C$_4$)alkylthio, (C$_1$-C$_4$)alkylsulfinyl, (C$_1$-C$_4$)alkylsulfonyl, (C$_1$-C$_4$)-alkanoyl, [(C$_1$-C$_4$)-alkoxy]-carbonyl, (C$_1$-C$_4$)alkylamino and di-[(C$_1$-C$_4$)alkyl]-amino, and heterocyclyl which is unsubstituted or substituted by one or more radicals selected from the group consisting of halogen, cyano, nitro, (C$_1$-C$_4$)alkyl, (C$_2$-C$_4$)alkenyl, (C$_2$-C$_4$)alkynyl, (C$_1$-C$_4$)haloalkyl, (C$_1$-C$_4$)alkoxy-(C$_1$-C$_4$)alkyl, (C$_1$-C$_4$)alkoxy, (C$_1$-C$_4$)haloalkoxy, (C$_1$-C$_4$)alkoxy-(C$_1$-C$_4$)alkoxy, (C$_1$-C$_4$)alkylthio, (C$_1$-C$_4$)alkylsulfinyl, (C$_1$-C$_4$)alkylsulfonyl, (C$_1$-C$_4$)-alkanoyl, [(C$_1$-C$_4$)alkoxy]carbonyl, (C$_1$-C$_4$)alkylamino and di[(C$_1$-C$_4$)alkyl]-amino, or is (C$_3$-C$_6$)cycloalkyl, phenyl or heterocyclyl, where each of the 3 latter radicals is optionally substituted, or, for example, is one of the eliminable radicals i) to xiii) mentioned, and R$^1$, independently of R$^0$, is (C$_1$-C$_6$)alkyl which is unsubstituted or substituted by one or more radicals selected from the group consisting of halogen, cyano, (C$_1$-C$_4$)alkoxy, (C$_1$-C$_4$)haloalkoxy, (C$_1$-C$_4$)alkylthio, aryl which is optionally substituted and heterocyclyl which is optionally substituted, or aryl which is optionally substituted or heterocyclyl which is optionally substituted, where the optionally substituted radicals are each independently preferably unsubstituted or substituted by one or more radicals selected from the group consisting of halogen, hydroxy, amino, cyano, nitro, (C$_1$-C$_4$)alkyl, (C$_3$-C$_9$)cycloalkyl, (C$_2$-C$_4$)alkenyl, (C$_5$-C$_9$)cycloalkenyl, (C$_2$-C$_4$)alkynyl, (C$_1$-C$_4$)alkoxy, (C$_1$-C$_5$)alkanoyl, [(C$_1$-C$_4$)alkoxy]carbonyl, (C$_1$-C$_4$)alkylthio, (C$_1$-C$_4$)alkylsulfonyl, (C$_1$-C$_4$)alkylamino, di(C$_1$-C$_4$)alkylamino, aryl and heterocyclyl, where the latter 14 radicals are each independently unsubstituted or substituted by one or more radicals selected from the group consisting of halogen, cyano, (C$_3$-C$_9$)cycloalkyl, (C$_5$-C$_9$)cycloalkenyl, (C$_1$-C$_4$)alkoxy, (C$_1$-C$_4$)alkylthio and, in the case of cyclic radicals, also (C$_1$-C$_4$)alkyl and (C$_1$-C$_4$)haloalkyl, and, preferably, R$^1$, independently of R$^0$, is (C$_1$-C$_6$)alkyl which is unsubstituted or substituted by one or more radicals selected from the group consisting of halogen, cyano, (C$_1$-C$_4$)alkoxy, (C$_1$-C$_4$)haloalkoxy and (C$_1$-C$_4$)alkylthio, or phenyl or heterocyclyl and R$^2$ is H, (C$_1$-C$_4$)alkyl, (C$_1$-C$_3$)haloalkyl, halogen, (C$_1$-C$_3$)alkoxy, (C$_1$-C$_3$)haloalkoxy or CN, R$^3$ is H, (C$_1$-C$_4$)alkyl, (C$_1$-C$_3$)haloalkyl, halogen, (C$_1$-C$_3$)alkoxy, (C$_1$-C$_3$)haloalkoxy or CN, R$^4$ is H, (C$_1$-C$_4$)alkyl, (C$_1$-C$_3$)haloalkyl, halogen, (C$_1$-C$_3$)alkoxy, (C$_1$-C$_3$)haloalkoxy or CN and R$^5$ is H, (C$_1$-C$_4$)alkyl, (C$_1$-C$_3$)haloalkyl, halogen, (C$_1$-C$_3$)alkoxy, (C$_1$-C$_3$)haloalkoxy or CN, where the substituents R$^1$ and the amino group on the two ring carbon atoms marked with an asterisk (*) in each case are arranged in cis arrangement to one another and the compound is present in the form of a stereochemically pure compound of the formula (Ib-A) or (Ib-B)

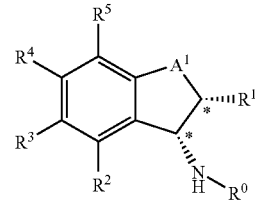

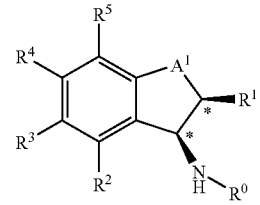

in which the general radicals are each as defined in formula (Ib), or in the form of an isomer mixture of the compounds of the formulae (Ib-A) and (Ib-B) in an isomer ratio other than the ratio of 1:1.

Preference is also given to processes for preparing bicyclic amino compounds of the formula (Ic)

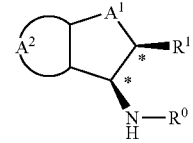

in which

A$^1$ is a direct bond or a group of the formula (CR$^6$R$^7$)$_n$ in which n is from 1 to 6 and R$^6$ and R$^7$ are each independently, or, in the case that n is greater than 1, the R$^6$ and R$^7$ radicals are in each case independently hydrogen, (C$_1$-C$_4$)alkyl, (C$_1$-C$_4$)haloalkyl, halogen, (C$_1$-C$_4$)alkoxy or (C$_1$-

$C_4$)haloalkoxy, where individual $CR^6R^7$ groups may be replaced by heteroatoms from the group of O and S, $A^2$, together with the two carbon atoms which are common with the other ring, is a carbocyclic nonaromatic ring which has from 3 to 9 carbon atoms and is unsubstituted or substituted by one or more radicals selected from the group consisting of ($C_1$-$C_4$)alkyl, ($C_1$-$C_3$)haloalkyl, halogen, ($C_1$-$C_3$)alkoxy, ($C_1$-$C_3$)haloalkoxy, hydroxy, amino and CN, $R^0$ is as defined above in formula (I), preferably as defined with preference for formula (I) and is in particular independently as defined in formula (Ib), and $R^1$ is independently as defined in formula (Ib), where the substituents $R^1$ and the amino group on the two ring carbon atoms marked with an asterisk (*) in each case are arranged in cis arrangement to one another and the compound (Ic) is present in the form of a stereochemically pure compound of the formula (Ic-A) or (Ic-B)

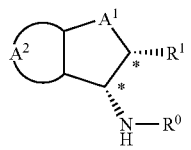
(Ic-A)

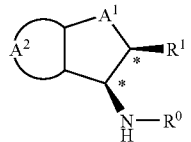
(Ic-B)

in which the general radicals are each as defined in formula (Ic), or in the form of an isomer mixture of the compounds of the formulae (Ic-A) and (Ic-B) in an isomer ratio other than the ratio of 1:1.

Preference is also given to processes for preparing bicyclic amino compounds of the formula (Id)

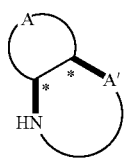
(Id)

in which

A, together with the carbon atoms designated with an asterisk (*) in each case, is a carbocyclic or heterocyclic, saturated or unsaturated, nonaromatic ring which has from 4 to 9 ring atoms, in particular from 5 to 7 ring atoms, and, in the case of a heterocyclic ring, has from 1 to 3 heterocyclic ring atoms from the group of N, O and S, and, in addition to the A' and NH—$R^0$ radicals, is unsubstituted or further substituted by one or more radicals selected from the group consisting of halogen, cyano, ($C_1$-$C_4$)alkyl, ($C_3$-$C_9$)cycloalkyl, ($C_1$-$C_4$)alkoxy and ($C_1$-$C_4$)alkylthio, where each of the latter 4 radicals is unsubstituted or substituted by one or more radicals selected from the group consisting of halogen, cyano, ($C_3$-$C_9$)cycloalkyl, ($C_1$-$C_4$)alkoxy, ($C_1$-$C_4$)alkylthio and, in the case of cyclic radicals, also ($C_1$-$C_4$)alkyl and ($C_1$-$C_4$)haloalkyl, and A' together with the NH group and the carbon atoms designated with an asterisk (*) in each case, is a heterocyclic ring which has from 4 to 9 ring atoms, in particular from 5 to 7 ring atoms, and optionally contains 1 or 2 further heteroatoms from the group of N, O and S and is unsubstituted or substituted by one or more radicals selected from the group consisting of halogen, cyano, ($C_1$-$C_4$)alkyl, ($C_1$-$C_4$)haloalkyl, ($C_1$-$C_4$)alkoxy, ($C_1$-$C_4$)haloalkoxy, ($C_1$-$C_4$)alkylthio and phenyl which is unsubstituted or substituted by one or more radicals selected from the group consisting of halogen, cyano, nitro, ($C_1$-$C_4$)alkyl, ($C_2$-$C_4$)alkenyl, ($C_2$-$C_4$)alkynyl, ($C_1$-$C_4$)haloalkyl, ($C_1$-$C_4$)alkoxy-($C_1$-$C_4$)alkyl, ($C_1$-$C_4$)alkoxy, ($C_1$-$C_4$)haloalkoxy, ($C_1$-$C_4$)alkoxy-($C_1$-$C_4$)alkoxy, ($C_1$-$C_4$)alkylthio, ($C_1$-$C_4$)alkylsulfinyl, ($C_1$-$C_4$)alkylsulfonyl, ($C_1$-$C_4$)alkanoyl, [($C_1$-$C_4$)alkoxy]carbonyl, ($C_1$-$C_4$)alkylamino and di[($C_1$-$C_4$)alkyl]amino, where the substituents A' and the amino group on the two ring carbon atoms marked with an asterisk (*) in each case are arranged in cis arrangement to one another and the compound (Id) is present in the form of a stereochemically pure compound of the formula (Id-A) or (Id-B)

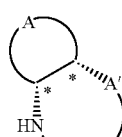
(Id-A)

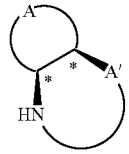
(Id-B)

in which the general radicals are each as defined in formula (Id), or in the form of an isomer mixture of the compounds of the formulae (Id-A) and (Id-B) in an isomer ratio other than the ratio of 1:1.

Preference is also given to processes for preparing bicyclic amino compounds of the formula (Ie)

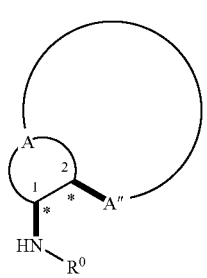
(Ie)

in which

A, together with the carbon atoms designated with an asterisk (*) in each case, is a carbocyclic or heterocyclic, saturated or unsaturated, nonaromatic ring which has from 4 to 9 ring atoms, in particular from 5 to 7 ring atoms, and, in the case of a heterocyclic ring, has from 1 to 3 heterocyclic ring atoms from the group of N, O and S, and, in addition to the A" and NH—$R^0$ radicals, is unsubstituted or further substituted by one or more radicals selected from the group consisting of halogen, cyano, $(C_1-C_4)$alkyl, $(C_3-C_9)$cycloalkyl, $(C_1-C_4)$alkoxy and $(C_1-C_4)$alkylthio, where each of the latter 4 radicals is unsubstituted or substituted by one or more radicals selected from the group consisting of halogen, cyano, $(C_3-C_9)$cycloalkyl, $(C_1-C_4)$alkoxy, $(C_1-C_4)$alkylthio and, in the case of cyclic radicals, also $(C_1-C_4)$alkyl and $(C_1-C_4)$haloalkyl, and A", together with the A and the carbon atom designated with "2" (=the carbon atom which is bonded to A" and is designated with an asterisk), is a carbocyclic or heterocyclic ring which has from 4 to 9 ring atoms, in particular from 5 to 7 ring atoms, and, in the heterocyclic case, contains 1 or 2 or 3 heteroatoms selected from the group consisting of N, O and S, and is unsubstituted or substituted by one or more radicals selected from the group consisting of halogen, hydroxy, amino, cyano, nitro, $(C_1-C_4)$alkyl, $(C_1-C_4)$haloalkyl, $(C_1-C_4)$alkoxy, $(C_1-C_4)$haloalkoxy, $(C_1-C_4)$alkylthio and phenyl which is unsubstituted or substituted by one or more radicals from the group of halogen, cyano, nitro, $(C_1-C_4)$alkyl, $(C_2-C_4)$alkenyl, $(C_2-C_4)$alkynyl, $(C_1-C_4)$haloalkyl, $(C_1-C_4)$alkoxy-$(C_1-C_4)$alkyl, $(C_1-C_4)$alkoxy, $(C_1-C_4)$haloalkoxy, $(C_1-C_4)$alkoxy-$(C_1-C_4)$alkoxy, $(C_1-C_4)$alkylthio, $(C_1-C_4)$alkylsulfinyl, $(C_1-C_4)$alkylsulfonyl, $(C_1-C_4)$-alkanoyl, $[(C_1-C_4)$alkoxy]-carbonyl, $(C_1-C_4)$alkylamino and di$[(C_1-C_4)$alkyl]amino, where $R^0$ is defined independently of A" as in the formulae (I), (Ia), (Ib) or (Ic), and the substituents A" and the amino group on the two ring carbon atoms marked with an asterisk (*) in each case are arranged in cis arrangement to one another and the compound (Ie) is present in the form of a stereochemically pure compound of the formula (Ie-A) or (Ie-B)

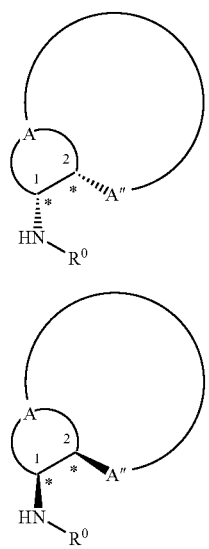

in which the general radicals are each as defined in formula (Ie), or in the form of an isomer mixture of the compounds of the formulae (Ie-A) and (Ie-B) in an isomer ratio other than the ratio of 1:1.

The reduction of the imino group of the compound (II) may be carried out analogously to processes as are known, for example, for the reduction of carbonyl compounds, or processes developed particularly therefor, as an asymmetric catalytic hydrogenation or catalytic transfer hydrogenation in the presence of hydrogen or hydrogen donors and chiral transition metal catalysts under reaction conditions under which chemical equilibrium between imine (II-A) and imine (II-B) is enabled.

Useful chiral catalysts for the reaction are those described analogously for asymmetric reductions of ketones, for example described in the references cited below or in the references cited in each of them:
Angew. Chem. Int. Ed. 2001 (40) p. 40-73,
Tetrahedron Lett. 1999 (40) 5043-5046,
J. Org. Chem. 1996, 61, 4872-4873
Angew. Chem. Int. Ed. 2004 (116) 806-843, specifically pages 829-830 and literature cited there,
Tetrahedron Asymmetry. 2003 (14) 1407-1446,
Org. Lett 1999 (1) 1119-1121,
Tetrahedron 2003 (59) 8291-8327.

Suitable catalysts for the reductions are, for example,
1. Ruthenium diphosphine 1,2-diamine complexes of the formula (1) and (2) and analogous complexes of the formulae (1') or (2') with other diamine bridges

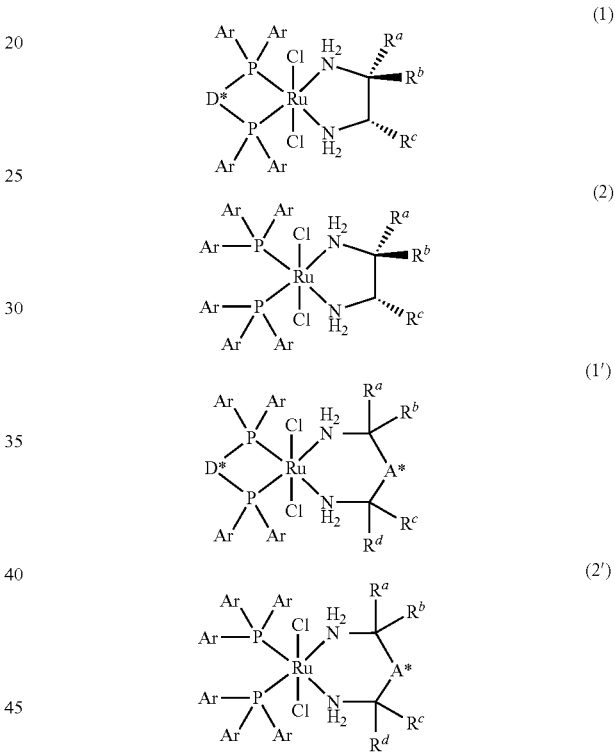

where, in each case,
Ar is an aryl radical, preferably phenyl radical, which is unsubstituted or substituted,
D* is a chiral organic group,
$R^a$, $R^b$, $R^c$ and $R^d$ are each hydrogen or optionally substituted aliphatic or aromatic groups which may also be joined to one another in pairs, where the 1,2-diamine bridge is chiral or achiral in the case of the compound (1) and is chiral in the case of the compound (2),
A* is alkylene having from 1 to 4 carbon atoms, preferably 2 carbon atoms, between the binding sites, where alkylene is optionally substituted, preferably unsubstituted, or is substituted by one or more radicals selected from the group consisting of halogen, $(C_1-C_4)$alkyl, $(C_1-C_4)$alkoxy, $(C_1-C_4)$alkylthio and $(C_1-C_4)$haloalkyl, or cycloalkylene which has from 3 to 6 carbon atoms and is unsubstituted or substituted by one or more radicals selected from the group consisting of halogen, $(C_1-C_4)$alkyl, $(C_1-C_4)$alkoxy, $(C_1-C_4)$alkylthio and $(C_1-C_4)$haloalkyl, preferably correspondingly optionally substituted 1,2-cycloalkylene, or a divalent heterocyclic radical which has from 3 to 6 ring atoms and 1, 2 or 3 heterocyclic ring atoms from the group of O, S and N, where the ring is unsubstituted or substituted by one or more radicals selected from the group consisting of halogen, $(C_1-C_4)$alkyl, $(C_1-C_4)$alkoxy, $(C_1-C_4)$alkylthio and $(C_1-C_4)$haloalkyl.

The compounds (1) and (2) or (1') and (2') may be prepared from ruthenium salts and the diphosphine bridge and diamine bridge compounds before the hydrogenation or in situ.

Examples of diphenylphosphine bridges $Ar_2P-D^*-PAr_2$ for preparing catalysts (1) or (1') are compounds of the formula (1a), (1b) and (1c):

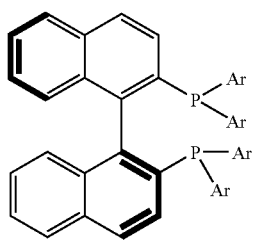
(1a)

especially the compounds:
(S)-BINAP: Ar=phenyl[1,1'-binaphthyl-2,2'-bis-(diphenylphosphine)]
(S)-TolBINAP: Ar=4-tolyl[1,1'-binaphthyl-2,2'-bis-(di-p-tolylphosphine)]
(S)-XylBINAP: Ar=3,5-xylyl[1,1'-binaphthyl-2,2'-bis-(di-m-xylylphosphine)] and correspondingly
(R)-BINAP, (R)-TolBINAP and (R)-XylBINAP

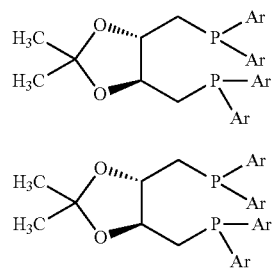
(1b)
(1c)

(1b) = (S,S)-DIOP
(1c) = (S,S)-CHIRAPHOS

Examples of chiral diamine bridges for the preparation of catalysts (1) and (2) or (1') and (2') are the following compounds:
(S,S)-DPEN=(1S,2S)-1,2-diamino-1,2-diphenylethane,
(S,S)-1,2-diaminocyclohexane,
(S)-DAIPEN=(2S)-1,2-diamino-1,1-bis-(4-methoxyphenyl)-3-methylbutane,
3,4-O-isopropylidene-(3S,4S)-dihydroxy-(2S,5S)-diaminohexane and correspondingly the enantiomeric compounds
(R,R)-DPEN, (R,R)-1,2-diaminocyclohexane, (R)-DAIPEN and
3,4-O-isopropylidene-(3R,4R)-dihydroxy-(2R,5R)-diaminohexane.

An example of a useful achiral diamine for preparing compounds (1) or (1') is 1,2-diaminoethane.

2. Corresponding to the ruthenium complexes specified under 1, it is also possible to use similar iridium complexes, for example $[Ir((R)-BINAP)(cod)]BF_4+P[C_6H_4-2-N(CH_3)_2]_2 C_6H_5$, where "cod" means the ligand cyclooctadiene.

3. Corresponding to the ruthenium complexes specified under 1, it is also possible to use similar iridium complexes, for example (R,S,R,S)-Me-PennPhos-Rh oxoProNOP—Rh 4. Metal complexes of the formula (3)

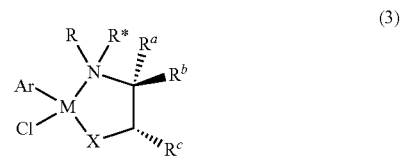
(3)

in which

M is a metal(II) ion from the group of Ru, Rh and Ir,

X is O or NR*R**,

Ar is an aryl radical, preferably phenyl, which is unsubstituted or substituted, especially alkylphenyl, $R^a$, $R^b$ and $R^c$ are optionally substituted aliphatic or aromatic groups which may also be joined to one another in pairs, the bridge being chiral, and R, R*, R and R* are each independently a free electron pair, H, alkyl or acyl, especially corresponding ruthenium(II) 1,2-diamine complexes.

5. Rhodium(III) and iridium(III) complexes of the formulae (4) and (5) which contain chiral ligands and their enantiomeric forms

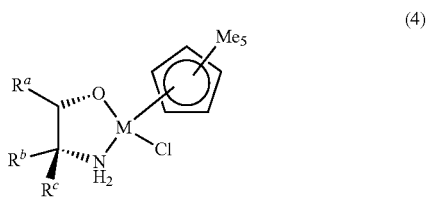
(4)

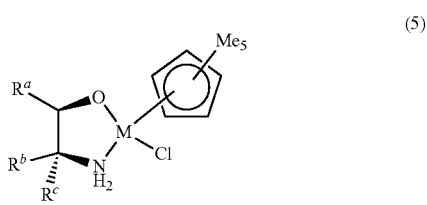
(5)

in which M is an Rh or Ir and $R^a$, $R^b$ and $R^c$ are each organic radicals. Some catalysts from this group are also commercially available (®Cathy catalysts from Avecia), for example rhodium(III) and iridium(III) complexes of the formulae (4a) or (4b) which contain chiral bicyclic ligands and their enantiomeric forms

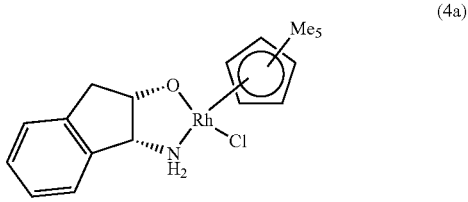
(4a)

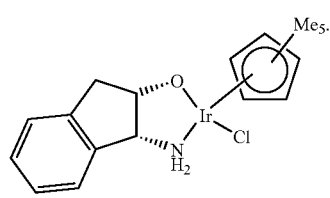

(4b)

The asymmetric hydrogenation can generally be carried out by hydrogenating the compound of the formula (II) in a suitable solvent in the presence of a suitable amount of the dissolved catalyst, optionally with addition of bases. The catalyst may optionally also be obtained in situ during the reaction from the components.

The hydrogenation may be effected, for example, as an asymmetric hydrogenation using hydrogen gas as a hydrogen donor or under conditions of asymmetric transfer hydrogenation with other hydrogen donors.

The quantitative ratio of compound (II) to catalyst may be varied within a wide range and is generally in the range from 100 000 mol to 10 mol of compound (II) per mole of the catalyst, preferably from 100 000 mol to 50 mol, in particular from 10 000 mol to 100 mol, of compound (II) per mole of the catalyst.

The suitable temperatures for the inventive reaction may be determined in preliminary experiments. They are generally within a temperature range of from −80° C. up to the boiling point of the mixture, preferably at temperatures of from 0° C. to 100° C., in particular from 15° C. to 60° C., very particularly at room temperature. The reaction is usually carried out at a hydrogen pressure of from 1 to 100 bar, preferably from 1 bar to 10 bar.

Suitable solvents for the catalytic hydrogenation are solvents inert under the reaction conditions, as are typically used in hydrogenation reactions, or mixtures thereof, for example alkanols such as methanol, ethanol, n-propanol, isopropanol, n-butanol, isobutanol, sec-butanol, t-butanol, water, carboxylic esters such as ethyl acetate, carboxylic acids such as glacial acetic acid, aromatic or aliphatic hydrocarbons such as benzene, toluene, xylene and paraffins, preferably toluene, xylene or mesitylene or else mixtures such as ®Solvesso (mineral oil mixture with aromatic fractions), halogenated aliphatic or aromatic hydrocarbons, for example chlorinated alkanes and alkenes, chlorobenzene, o-dichlorobenzene, nitriles such as acetonitrile, ethers such as diethyl ether or cyclic ethers such as dioxane or tetrahydrofuran, amides such as dimethylformamide, sulfones such as sulfolane, and mixtures of the solvents mentioned.

As a variant of the hydrogenation, an asymmetric transfer hydrogenation may be carried out with a hydrogen donor in the presence of the above-described catalysts. Suitable hydrogen donors are compounds which can themselves be oxidized under the conditions. Suitable hydrogen donors are, for example, formic acid and its salts, as are also used for the performance of the Leukart-Wallach reaction (see, for example, Houben-Weyl 11/1, 648-664 and Synthesis 1988, 92 and literature cited there). A suitable hydrogen donor is thus formic acid which can be used optionally in combination with a base, for example a tertiary amine base. Bases are, for example, ammonia or primary, secondary and tertiary amines, for example those with alkyl, aralkyl and/or aryl radicals, preferably corresponding amines with $(C_1-C_4)$alkyl radicals. Suitable salts are corresponding (substituted) ammonium formates. Further hydrogen donors are isopropanol or cyclohexadiene (cf. Adv. Synth. Catal. 2003, Vol. 345, pages 67-77, Tetrahedron: Asymmetry 10 (1999) 2045-2061, Eur. J. Inorg. Chem. 2002, 2239-2251), also in each case in combination with the catalysts mentioned specifically in the references.

Preference is given to the use of catalysts of the abovementioned formulae (3), (4) and (5) in combination with formic acid and tertiary amines such as triethylamine.

Suitable mixing ratios of formic acid:amine are from 10:1 to 1:10 based on the weight. The donor system may be used directly as a solvent or be used in a mixture with other solvents as cosolvents.

Suitable solvents for the catalytic transfer hydrogenation are solvents inert under the reaction conditions or mixtures thereof, for example alkanols such as methanol, ethanol, n-propanol, isopropanol, n-butanol, isobutanol, sec-butanol, t-butanol, water, carboxylic esters such as ethyl acetate, carboxylic acids such as glacial acetic acid, aromatic or aliphatic hydrocarbons such as benzene, toluene, xylene and paraffins, preferably toluene, xylene or mesitylene or else mixtures such as ®Solvesso (mineral oil mixture with aromatic fractions), halogenated aliphatic or aromatic hydrocarbons, for example chlorinated alkanes and alkenes, chlorobenzene, o-dichlorobenzene, nitriles such as acetonitrile, ethers such as diethyl ether or cyclic ethers such as dioxane or tetrahydrofuran, amides such as dimethylformamide, sulfones such as sulfolane, and mixtures of the solvents mentioned.

The catalytic hydrogenation and the catalytic transfer hydrogenation may be carried out analogously to the customary conditions, as described in the literature mentioned for the reduction of ketones to optically active alcohols.

The performance of the reaction with regard to amount of catalyst and reaction time should be optimized in preliminary experiments in order to achieve a high conversion rate, chemical yield and enantiomeric excess.

Surprisingly, it is possible in the hydrogenations to achieve good enantioselectivity of the amine (I) not only with regard to the chiral center at which the amino group is bonded but also with regard to the adjacent chiral center.

The starting materials of the formula (II) are known or can be prepared analogously to known processes. A simple possibility is the preparation via the corresponding ketone. Cyclic ketones are in many cases commercially available or can be prepared by a large number of reactions known to those skilled in the art from other compounds such as alcohols, halogen compounds, or from esters or carboxylic acids by ring-closure reactions. Bicyclic ketones are, for example, also described in WO 97/031904 and WO 2004/069814.

A particular means of preparing the optically active amines (I) and their salts also consists in carrying out a two-stage process with in situ preparation of the imine from a corresponding ketone and direct reduction in the presence of the catalyst. The imine is formed by reaction of the ketone with a suitable amount of a primary amine $R^0$—$NH_2$ where $R^0$ is as defined in formula (I) and is reduced to the amine without intermediate isolation. The in situ process can be carried out, for example, with an amount of from 0.1 mol up to a severalfold excess of primary amine per mole of ketone, preferably from 1 to 10 mol, in particular from 1 to 5 mol, more preferably from 1 to 2 mol, of primary amine per mole of ketone. The two-stage reaction can generally be controlled by adding the optically active catalyst. The temperature conditions depend substantially upon the suitable temperature for the catalytic reaction.

The resulting compounds of the formula (I) are suitable as optically active synthons for preparing optically active active ingredients. A particularly frequent use of the compounds (I) and their salts is the preparation of the corresponding free amines (I'), the difference of the formula (I') from the formula (I) consisting in the replacement of the $R^0$ radical by hydrogen.

The free optically active cis-amines of the formula (I') and their salts therefore likewise form part of the subject matter of the invention. They can be prepared from suitable compounds of the formula (I) by standard reactions, for example by elimination of protecting groups $R^0$ for which an elimination reaction, preferably a gentle elimination reaction, is known. Examples of such eliminable groups are the groups i)-xv) mentioned above. The preparation of these groups and their common and preferred elimination methods are described, for example, in the handbook "Protective Groups in Organic Synthesis, $3^{rd}$ ed., T. W. Greene and P. G. M. Wuts; 1999, John Wiley & Sons, Inc. (see in particular pages 575 to 585) and literature cited there.

The experiments are illustrated in detail by the examples which follow without any intention that the invention be restricted to these embodiments. Amounts are based on weight unless stated otherwise.

ABBREVIATIONS IN THE EXAMPLES

Me=methyl
Et=ethyl
n- or i-Pr or t-butyl=n-propyl or isopropyl or t-butyl
Ph=phenyl
Ts=p-tosyl=p-tolylsulfonyl
Allyl=$CH_2$—CH=$CH_2$
Bzl=benzyl =$CH_2Ph$
p-MeO-Bzl=para-methoxybenzyl=(p-methoxyphenyl)methyl

EXAMPLE A1 cis-(S,S)-Benzyl-(2-methyl-1,2,3,4-tetrahydronaphth-1-yl)amine

A1a) Preparation of the catalyst Ru(p-cymene)-(S,S)-TsDPEN

Bis(p-cymeneruthenium dichloride) is initially charged in an organic solvent and reacted at room temperature with (S,S)-TsDPEN [(S,S)-N-tosyl-1,2-diamino-1,2-diphenylethane]. Concentration and removal of the solvent under high vacuum affords Ru(p-cymene)(S,S)-TsDPEN of the formula:

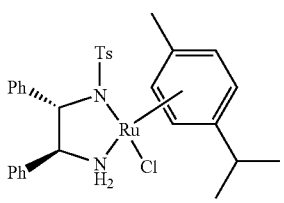

Correspondingly, the compound Ru(p-cymene)(R,R)-TsDPEN is obtained using (R,R)-TsDPEN.

A1b) (1S,2S)-N-Benzyl-(2-methyl-1,2,3,4-tetrahydronaphth-1-yl)amine 3 mg (4.7 µmol) of the catalyst from example A1a are dissolved in 1 ml of a mixture of formic acid and triethylamine (5:2 v/v) and stirred for 20 min. A solution of 350 mg (1.141 mmol) of racemic N-benzyl-(2-methyl-3,4-dihydro-2H-naphth-1-ylidene)amine in 1.7 ml of dichloromethane is then added and the mixture is stirred at room temperature for 5 days. After removal of the solvent, the dissolution in 5 ml of methanol, treatment with approx. 200 mg of potassium hydroxide and admixing with 10 ml of water at room temperature, extraction is effected three times with in each case 15 ml of dichloromethane and the organic phase is dried over sodium sulfate. After removal of the solvent and column chromatography (20:1 hexane/ethyl acetate), 229 mg (65% yield) of (1S,2S)-N-benzyl-(2-methyl-1,2,3,4-tetrahydronaphth-1-yl)amine are obtained as a light yellow oil.

$[\alpha]^{21}_D$=−31.1° (c 0.8, $CHCl_3$); $^1H$ NMR (400 MHz, $C_6D_6$) δ=6.98-7.22 (m, 9H), 3.75 (d, 1H, J=14.0 Hz), 3.71 (d, 1H, J=14.0 Hz), 3.47 (d, 1H, J=3.6 Hz), 2.68 (dt, 1H, J=17.2, 5.6 Hz), 2.55 (dt, 1H, J=16.8, 8.0 Hz), 1.84 (m, 4H), 1.63 (m, 1H), 1.48 (m, 1H), 0.95 (d, 3H, J=6.5 Hz), $^{13}C$ NMR (100 MHz, $C_6D_6$) δ=141.8, 140.2, 136.5, 129.5, 129.2, 128.7, 128.6, 127.2, 127.0, 125.8, 259.3, 52.6, 32.5, 28.0, 26.5, 16.5. The enantiomeric excess (ee %) was determined by chromatography (ee=98%); HPLC on Chiralpak AD (Daicel), 96:4 n-hexane:isopropanol, 30° C., flow rate: 0.5 ml/min; RT: 7.07 min.

EXAMPLE A2

(1R,2S)-N-Allyl-(2-methylcyclohexyl)amine

A solution of 22.5 mg (35 µmol) of the catalyst from example A1a in 3.2 ml of a mixture of formic acid and triethylamine (5:2 v/v) is added dropwise to a mixture of 676 mg (6 mmol) of 2-methylcyclohexanone, 2.74 g (48 mmol) of allylamine and 100 mg of magnesium sulfate, and stirred. After 7 days at room temperature, the reaction mixture is diluted with 20 ml of water and extracted three times with 15 ml of dichloromethane. The organic phase is dried over sodium sulfate. After removal of the solvent and column chromatography (silica gel, 10:1 dichloromethane/methanol), 708 mg (77% yield) of (1R,2S)-N-allyl-(2-methylcyclohexyl)amine are obtained.

$[\alpha]^{21}_D$=+8.2° (c 0.7, $CHCl_3$); $^1H$ NMR (300 MHz, $CDCl_3$) δ=5.88 (m, 1H), 5.14 (dd, 1H, J=1.6, 16.2 Hz), 5.03 (m, 1H), 3.19 (m, 1H), 2.58 (m, 1H), 1.90 (m, 1H), 1.7-1.2 (m, 9H), 0.86 (d, 1H, J=7.0 Hz),
$^{13}C$ NMR (75 MHz) δ=137.8, 115.8, 58.8, 49.9, 31.4, 28.4, 24.1, 22.2, 19.6, 13.8.

The enantiomeric excess (ee %) was determined by chromatography (ee=95.9%); HPLC on Chiralpak OJ (Daicel), 99.5:0.5 n-hexane:isopropanol, 30° C., flow rate: 0.5 ml/min; RT: 17.16 min.

EXAMPLE A3

(1R,2R)-N-Benzyl-(2-phenylcyclohexyl)amine 16.6 mg of IrCl[(S,S)-TsDPEN]Cp* and a solution of racemic 1-benzyl-N-[2-phenylcyclohexylidene]amine in 10 ml of dry dichloromethane are added to 3.2 ml of a mixture of formic acid and triethylamine (5:2 v/v). After stirring at room temperature for 24 h, the mixture is diluted with 0.5 M aq. $Na_2CO_3$ until pH 10 is attained and then extracted with dichloromethane (2×30 ml). The organic phase is subsequently dried over magnesium sulfate and concentrated under reduced pressure, and the residue is purified by column chromatography (silica gel, 1:12 ethyl acetate/hexane). (1R,2R)-N-Benzyl-(2-phenylcyclohexyl)amine is obtained in 60% yield. $[\alpha]^{22}_D$=+33.4° (c 0.7, CHCl$_3$); $^1$H NMR (300 MHz, CDCl$_3$) δ=6.9-7.4 (m, 10H), 3.68 (d, J=13.8 Hz, 1H), 3.0 (m, 1H), 2.85 (dt, J=13.3, 3.2 Hz), 1H), 1.1-2.2 (m, 8H);

$^{13}$C NMR (75 MHz) δ=143.9, 140.3, 127.7, 127.5, 127.1, 125.9, 125.5, 56.1, 50.7, 46.5, 29.2, 25.9, 24.1, 19.1. The diastereomeric excess (de) was determined by means of $^1$H-NMR (de>98%). The enantiomeric excess was determined after debenzylation and subsequent acetylation of the released amino function (ee=50%).

According to examples A1, A2 and A3 and the variants mentioned in the description, the example compounds mentioned in the following tables 1 and 2 are also obtained.

Comments on Tables 1 and 2:

Methods for determining the retention time by HPLC on chiral phase. All measurements with n-hexane/isopropanol as eluent at 30° C. References reported as follows: R$_t$ (min), eluent and flow rate (v$_{nHex}$/v$_{iProH}$-ml/min)

$^{(1)}$ Chiralpak AD (Daicel)
$^{(2)}$ Chiralpak OJ (Daicel)
$^{(3)}$ Chiralpak OB (Daicel)
$^{(4)}$ characterized as the N-benzoyl derivative Some data on the compounds are reported at the end of each table.

TABLE 1

Compounds of the formula (Ia-A) and (Ia-B)

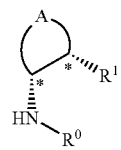

(Ia-A)

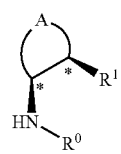

(Ia-B)

The numbers in the first column of the table relate to the compounds of the formula (Ia-A) with the substituent definitions in the columns under A, R$^0$ and R$^1$. Correspondingly, the numbers in the second column relate to the compounds of the formula (Ia-B) with the substituent definitions in the columns under A, R$^0$ and R$^1$.

| Comp. (Ia-A) No. | Comp. (Ia-B) No. | A | R$^0$ | R$^1$ |
|---|---|---|---|---|
| aA1 | aB1 | CH$_2$ | Me | Me |
| aA2 | aB2 | CH$_2$CH$_2$ | Me | Me |
| aA3 | aB3 | CH$_2$CH$_2$CH$_2$ | Me | Me |
| aA4 | aB4 | CH$_2$CH$_2$CH$_2$CH$_2$ | Me | Me |
| aA5 | aB5 | CH$_2$CH$_2$CH$_2$CH$_2$CH$_2$ | Me | Me |
| aA6 | aB6 | CH$_2$O | Me | Me |
| aA7 | aB7 | CH$_2$OCH$_2$ | Me | Me |
| aA8 | aB8 | CH$_2$ | Me | Et |
| aA9 | aB9 | CH$_2$ | Me | n-Pr |
| aA10 | aB10 | CH$_2$CH$_2$ | Me | Et |
| aA11 | aB11 | CH$_2$CH$_2$ | Me | n-Pr |
| aA12 | aB12 | CH$_2$CH$_2$CH$_2$ | Me | Et |
| aA13 | aB13 | CH$_2$CH$_2$CH$_2$ | Me | n-Pr |
| aA14 | aB14 | CH$_2$CH$_2$CH$_2$CH$_2$ | Me | Et |
| aA15 | aB15 | CH$_2$CH$_2$CH$_2$CH$_2$ | Me | n-Pr |
| aA16 | aB16 | CH$_2$CH$_2$CH$_2$CH$_2$CH$_2$ | Me | Et |
| aA17 | aB17 | CH$_2$CH$_2$CH$_2$CH$_2$CH$_2$ | Me | n-Pr |
| aA18 | aB18 | CH$_2$O | Me | Et |
| aA19 | aB19 | CH$_2$O | Me | n-Pr |
| aA20 | aB20 | CH$_2$OCH$_2$ | Me | Et |
| aA21 | aB21 | CH$_2$OCH$_2$ | Me | n-Pr |
| aA22 | aB22 | CH$_2$ | Et | Me |
| aA23 | aB23 | CH$_2$CH$_2$ | Et | Me |
| aA24 | aB24 | CH$_2$CH$_2$CH$_2$ | Et | Me |
| aA25 | aB25 | CH$_2$CH$_2$CH$_2$CH$_2$ | Et | Me |
| aA26 | aB26 | CH$_2$CH$_2$CH$_2$CH$_2$CH$_2$ | Et | Me |
| aA27 | aB27 | CH$_2$O | Et | Me |
| aA28 | aB28 | CH$_2$OCH$_2$ | Et | Me |
| aA29 | aB29 | CH$_2$ | Et | Et |
| aA30 | aB30 | CH$_2$ | Et | n-Pr |
| aA31 | aB31 | CH$_2$CH$_2$ | Et | Et |
| aA32 | aB32 | CH$_2$CH$_2$ | Et | n-Pr |
| aA33 | aB33 | CH$_2$CH$_2$CH$_2$ | Et | Et |
| aA34 | aB34 | CH$_2$CH$_2$CH$_2$ | Et | n-Pr |
| aA35 | aB35 | CH$_2$CH$_2$CH$_2$CH$_2$ | Et | Et |
| aA36 | aB36 | CH$_2$CH$_2$CH$_2$CH$_2$ | Et | n-Pr |
| aA37 | aB37 | CH$_2$CH$_2$CH$_2$CH$_2$CH$_2$ | Et | Et |
| aA38 | aB38 | CH$_2$CH$_2$CH$_2$CH$_2$CH$_2$ | Et | n-Pr |
| aA39 | aB39 | CH$_2$O | Et | Et |
| aA40 | aB40 | CH$_2$O | Et | n-Pr |
| aA41 | aB41 | CH$_2$OCH$_2$ | Et | Et |
| aA42 | aB42 | CH$_2$OCH$_2$ | Et | n-Pr |
| aA43 | aB43 | CH$_2$ | Allyl | Me |
| aA44 | aB44 | CH$_2$CH$_2$ | Allyl | Me |
| aA45 | aB45 | CH$_2$CH$_2$CH$_2$ | Allyl | Me |
| aA46 | aB46 | CH$_2$CH$_2$CH$_2$CH$_2$ | Allyl | Me |
| aA47 | aB47 | CH$_2$CH$_2$CH$_2$CH$_2$CH$_2$ | Allyl | Me |
| aA48 | aB48 | CH$_2$O | Allyl | Me |
| aA49 | aB49 | CH$_2$OCH$_2$ | Allyl | Me |
| aA50 | aB50 | CH$_2$ | Allyl | Et |
| aA51 | aB51 | CH$_2$ | Allyl | n-Pr |
| aA52 | aB52 | CH$_2$CH$_2$ | Allyl | Et |
| aA53 | aB53 | CH$_2$CH$_2$ | Allyl | n-Pr |
| aA54 | aB54 | CH$_2$CH$_2$CH$_2$ | Allyl | Et |
| aA55 | aB55 | CH$_2$CH$_2$CH$_2$ | Allyl | n-Pr |
| aA56 | aB56 | CH$_2$CH$_2$CH$_2$CH$_2$ | Allyl | Et |
| aA57 | aB57 | CH$_2$CH$_2$CH$_2$CH$_2$ | Allyl | n-Pr |
| aA58 | aB58 | CH$_2$CH$_2$CH$_2$CH$_2$CH$_2$ | Allyl | Et |
| aA59 | aB59 | CH$_2$CH$_2$CH$_2$CH$_2$CH$_2$ | Allyl | n-Pr |
| aA60 | aB60 | CH$_2$O | Allyl | Et |
| aA61 | aB61 | CH$_2$O | Allyl | n-Pr |
| aA62 | aB62 | CH$_2$OCH$_2$ | Allyl | Et |
| aA63 | aB63 | CH$_2$OCH$_2$ | Allyl | n-Pr |
| aA64 | aB64 | CH$_2$ | Bzl | Me |
| aA65 | aB65 | CH$_2$CH$_2$ | Bzl | Me |
| aA66 | aB66 | CH$_2$CH$_2$CH$_2$ | Bzl | Me |
| aA67 | aB67 | CH$_2$CH$_2$CH$_2$ | Bzl | Me |
| aA68 | aB68 | CH$_2$CH$_2$CH$_2$CH$_2$ | Bzl | Me |
| aA69 | aB69 | CH$_2$O | Bzl | Me |
| aA70 | aB70 | CH$_2$OCH$_2$ | Bzl | Me |

TABLE 1-continued

Compounds of the formula (Ia-A) and (Ia-B)

(Ia-A)

(Ia-B)

The numbers in the first column of the table relate to the compounds of the formula (Ia-A) with the substituent definitions in the columns under A, $R^0$ and $R^1$. Correspondingly, the numbers in the second column relate to the compounds of the formula (Ia-B) with the substituent definitions in the columns under A, $R^0$ and $R^1$.

| Comp. (Ia-A) No. | Comp. (Ia-B) No. | A | $R^0$ | $R^1$ |
|---|---|---|---|---|
| aA71 | aB71 | $CH_2$ | Bzl | Et |
| aA72 | aB72 | $CH_2$ | Bzl | n-Pr |
| aA73 | aB73 | $CH_2$ | Bzl | Ph |
| aA74 | aB74 | $CH_2CH_2$ | Bzl | Et |
| aA75 | aB75 | $CH_2CH_2$ | Bzl | n-Pr |
| aA76 | aB76 | $CH_2CH_2$ | Bzl | Ph |
| aA77 | aB77 | $CH_2CH_2CH_2$ | Bzl | Et |
| aA78 | aB78 | $CH_2CH_2CH_2$ | Bzl | n-Pr |
| aA79 | aB79 | $CH_2CH_2CH_2$ | Bzl | Ph |
| aA80 | aB80 | $CH_2CH_2CH_2CH_2$ | Bzl | Et |
| aA81 | aB81 | $CH_2CH_2CH_2CH_2$ | Bzl | n-Pr |
| aA82 | aB82 | $CH_2CH_2CH_2CH_2$ | Bzl | Ph |
| aA83 | aB83 | $CH_2CH_2CH_2CH_2CH_2$ | Bzl | Et |
| aA84 | aB84 | $CH_2CH_2CH_2CH_2CH_2$ | Bzl | n-Pr |
| aA85 | aB85 | $CH_2CH_2CH_2CH_2CH_2$ | Bzl | Ph |
| aA86 | aB86 | $CH_2O$ | Bzl | Et |
| aA87 | aB87 | $CH_2O$ | Bzl | n-Pr |
| aA88 | aB88 | $CH_2O$ | Bzl | Ph |
| aA89 | aB89 | $CH_2OCH_2$ | Bzl | Et |
| aA90 | aB90 | $CH_2OCH_2$ | Bzl | n-Pr |
| aA91 | aB91 | $CH_2OCH_2$ | Bzl | Ph |

Physical data on compounds from table 1:
Compound No.: aB46: Ref[2,4] $R_f$ = 17.2, n-hexane/isopropanol = 99.5:0.5 (v/v), flow rate = 0.5 ml/mm

TABLE 2

Compounds of the formula (Ib-A) and (Ib-B)

(Ib-A)

(Ib-B)

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA1 | bB1 | — | Me | Me | H | H | H | H |
| bA2 | bB2 | — | Me | Me | Me | H | H | H |

TABLE 2-continued

Compounds of the formula (Ib-A) and (Ib-B)

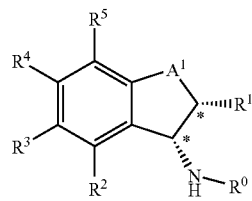
(Ib-A)

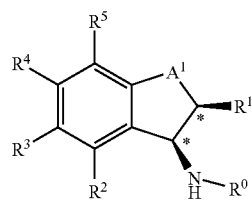
(Ib-B)

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA3 | bB3 | — | Me | Me | H | Me | H | H |
| bA4 | bB4 | — | Me | Me | H | H | Me | H |
| bA5 | bB5 | — | Me | Me | H | H | H | Me |
| bA6 | bB6 | — | Me | Me | Cl | H | H | H |
| bA7 | bB7 | — | Me | Me | H | Cl | H | H |
| bA8 | bB8 | — | Me | Me | H | H | Cl | H |
| bA9 | bB9 | — | Me | Me | H | H | H | Cl |
| bA10 | bB10 | — | Me | Me | Et | H | H | H |
| bA11 | bB11 | — | Me | Me | H | Et | H | H |
| bA12 | bB12 | — | Me | Me | H | H | Et | H |
| bA13 | bB13 | — | Me | Me | H | H | H | Et |
| bA14 | bB14 | — | Me | Me | OMe | H | H | H |
| bA15 | bB15 | — | Me | Me | H | OMe | H | H |
| bA16 | bB16 | — | Me | Me | H | H | OMe | H |
| bA17 | bB17 | — | Me | Me | H | H | H | OMe |
| bA18 | bB18 | — | Me | Me | F | H | H | H |
| bA19 | bB19 | — | Me | Me | H | F | H | H |
| bA20 | bB20 | — | Me | Me | H | H | F | H |
| bA21 | bB21 | — | Me | Me | H | H | H | F |
| bA22 | bB22 | — | Et | Me | H | H | H | H |
| bA23 | bB23 | — | Et | Me | Me | H | H | H |
| bA24 | bB24 | — | Et | Me | H | Me | H | H |
| bA25 | bB25 | — | Et | Me | H | H | Me | H |
| bA26 | bB26 | — | Et | Me | H | H | H | Me |
| bA27 | bB27 | — | Et | Me | Cl | H | H | H |
| bA28 | bB28 | — | Et | Me | H | Cl | H | H |
| bA29 | bB29 | — | Et | Me | H | H | Cl | H |
| bA30 | bB30 | — | Et | Me | H | H | H | Cl |
| bA31 | bB31 | — | Et | Me | Et | H | H | H |
| bA32 | bB32 | — | Et | Me | H | Et | H | H |
| bA33 | bB33 | — | Et | Me | H | H | Et | H |
| bA34 | bB34 | — | Et | Me | H | H | H | Et |
| bA35 | bB35 | — | Et | Me | OMe | H | H | H |
| bA36 | bB36 | — | Et | Me | H | OMe | H | H |
| bA37 | bB37 | — | Et | Me | H | H | OMe | H |
| bA38 | bB38 | — | Et | Me | H | H | H | OMe |
| bA39 | bB39 | — | Et | Me | F | H | H | H |
| bA40 | bB40 | — | Et | Me | H | F | H | H |
| bA41 | bB41 | — | Et | Me | H | H | F | H |
| bA42 | bB42 | — | Et | Me | H | H | H | F |
| bA43 | bB43 | — | Allyl | Me | H | H | H | H |
| bA44 | bB44 | — | Allyl | Me | Me | H | H | H |
| bA45 | bB45 | — | Allyl | Me | H | Me | H | H |
| bA46 | bB46 | — | Allyl | Me | H | H | Me | H |
| bA47 | bB47 | — | Allyl | Me | H | H | H | Me |
| bA48 | bB48 | — | Allyl | Me | Cl | H | H | H |
| bA49 | bB49 | — | Allyl | Me | H | Cl | H | H |
| bA50 | bB50 | — | Allyl | Me | H | H | Cl | H |

TABLE 2-continued

Compounds of the formula (Ib-A) and (Ib-B)

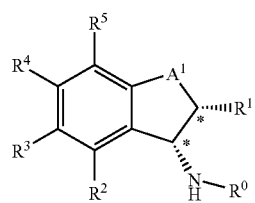
(Ib-A)

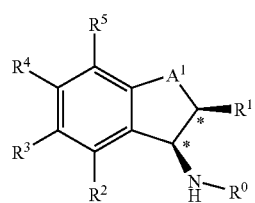
(Ib-B)

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA51 | bB51 | — | Allyl | Me | H | H | H | Cl |
| bA52 | bB52 | — | Allyl | Me | Et | H | H | H |
| bA53 | bB53 | — | Allyl | Me | H | Et | H | H |
| bA54 | bB54 | — | Allyl | Me | H | H | Et | H |
| bA55 | bB55 | — | Allyl | Me | H | H | H | Et |
| bA56 | bB56 | — | Allyl | Me | OMe | H | H | H |
| bA57 | bB57 | — | Allyl | Me | H | OMe | H | H |
| bA58 | bB58 | — | Allyl | Me | H | H | OMe | H |
| bA59 | bB59 | — | Allyl | Me | H | H | H | OMe |
| bA60 | bB60 | — | Allyl | Me | F | H | H | H |
| bA61 | bB61 | — | Allyl | Me | H | F | H | H |
| bA62 | bB62 | — | Allyl | Me | H | H | F | H |
| bA63 | bB63 | — | Allyl | Me | H | H | H | F |
| bA64 | bB64 | — | Bzl | Me | H | H | H | H |
| bA65 | bB65 | — | Bzl | Me | Me | H | H | H |
| bA66 | bB66 | — | Bzl | Me | H | Me | H | H |
| bA67 | bB67 | — | Bzl | Me | H | H | Me | H |
| bA68 | bB68 | — | Bzl | Me | H | H | H | Me |
| bA69 | bB69 | — | Bzl | Me | Cl | H | H | H |
| bA70 | bB70 | — | Bzl | Me | H | Cl | H | H |
| bA71 | bB71 | — | Bzl | Me | H | H | Cl | H |
| bA72 | bB72 | — | Bzl | Me | H | H | H | Cl |
| bA73 | bB73 | — | Bzl | Me | Et | H | H | H |
| bA74 | bB74 | — | Bzl | Me | H | Et | H | H |
| bA75 | bB75 | — | Bzl | Me | H | H | Et | H |
| bA76 | bB76 | — | Bzl | Me | H | H | H | Et |
| bA77 | bB77 | — | Bzl | Me | OMe | H | H | H |
| bA78 | bB78 | — | Bzl | Me | H | OMe | H | H |
| bA79 | bB79 | — | Bzl | Me | H | H | OMe | H |
| bA80 | bB80 | — | Bzl | Me | H | H | H | OMe |
| bA81 | bB81 | — | Bzl | Me | F | H | H | H |
| bA82 | bB82 | — | Bzl | Me | H | F | H | H |
| bA83 | bB83 | — | Bzl | Me | H | H | F | H |
| bA84 | bB84 | — | Bzl | Me | H | H | H | F |
| bA85 | bB85 | — | p-MeO-Bzl | Me | H | H | H | H |
| bA86 | bB86 | — | p-MeO-Bzl | Me | Me | H | H | H |
| bA87 | bB87 | — | p-MeO-Bzl | Me | H | Me | H | H |
| bA88 | bB88 | — | p-MeO-Bzl | Me | H | H | Me | H |
| bA89 | bB89 | — | p-MeO-Bzl | Me | H | H | H | Me |
| bA90 | bB90 | — | p-MeO-Bzl | Me | Cl | H | H | H |
| bA91 | bB91 | — | p-MeO-Bzl | Me | H | Cl | H | H |
| bA92 | bB92 | — | p-MeO-Bzl | Me | H | H | Cl | H |
| bA93 | bB93 | — | p-MeO-Bzl | Me | H | H | H | Cl |
| bA94 | bB94 | — | p-MeO-Bzl | Me | Et | H | H | H |
| bA95 | bB95 | — | p-MeO-Bzl | Me | H | Et | H | H |
| bA96 | bB96 | — | p-MeO-Bzl | Me | H | H | Et | H |
| bA97 | bB97 | — | p-MeO-Bzl | Me | H | H | H | Et |
| bA98 | bB98 | — | p-MeO-Bzl | Me | OMe | H | H | H |

TABLE 2-continued

Compounds of the formula (Ib-A) and (Ib-B)

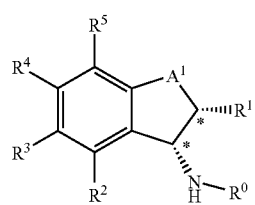
(Ib-A)

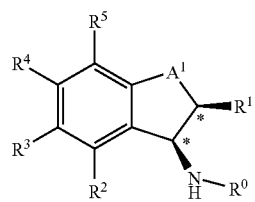
(Ib-B)

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA99 | bB99 | — | p-MeO-Bzl | Me | H | OMe | H | H |
| bA100 | bB100 | — | p-MeO-Bzl | Me | H | H | OMe | H |
| bA101 | bB101 | — | p-MeO-Bzl | Me | H | H | H | OMe |
| bA102 | bB102 | — | p-MeO-Bzl | Me | F | H | H | H |
| bA103 | bB103 | — | p-MeO-Bzl | Me | H | F | H | H |
| bA104 | bB104 | — | p-MeO-Bzl | Me | H | H | F | H |
| bA105 | bB105 | — | p-MeO-Bzl | Me | H | H | H | F |
| bA106 | bB106 | — | i-Pr | Me | Me | H | H | H |
| bA107 | bB107 | — | i-Pr | Me | H | Me | H | H |
| bA108 | bB108 | — | i-Pr | Me | H | H | Me | H |
| bA109 | bB109 | — | i-Pr | Me | H | H | H | Me |
| bA110 | bB110 | — | i-Pr | Me | Cl | H | H | H |
| bA111 | bB111 | — | i-Pr | Me | H | Cl | H | H |
| bA112 | bB112 | — | i-Pr | Me | H | H | Cl | H |
| bA113 | bB113 | — | i-Pr | Me | H | H | H | Cl |
| bA114 | bB114 | — | i-Pr | Me | Et | H | H | H |
| bA115 | bB115 | — | i-Pr | Me | H | Et | H | H |
| bA116 | bB116 | — | i-Pr | Me | H | H | Et | H |
| bA117 | bB117 | — | i-Pr | Me | H | H | H | Et |
| bA118 | bB118 | — | i-Pr | Me | OMe | H | H | H |
| bA119 | bB119 | — | i-Pr | Me | H | OMe | H | H |
| bA120 | bB120 | — | i-Pr | Me | H | H | OMe | H |
| bA121 | bB121 | — | i-Pr | Me | H | H | H | OMe |
| bA122 | bB122 | — | i-Pr | Me | F | H | H | H |
| bA123 | bB123 | — | i-Pr | Me | H | F | H | H |
| bA124 | bB124 | — | i-Pr | Me | H | H | F | H |
| bA125 | bB125 | — | i-Pr | Me | H | H | H | F |
| bA126 | bB126 | — | t-Bu | Me | H | H | H | H |
| bA127 | bB127 | — | t-Bu | Me | Me | H | H | H |
| bA128 | bB128 | — | t-Bu | Me | Me | Me | H | H |
| bA129 | bB129 | — | t-Bu | Me | H | H | Me | H |
| bA130 | bB130 | — | t-Bu | Me | H | H | H | Me |
| bA131 | bB131 | — | t-Bu | Me | Cl | H | H | H |
| bA132 | bB132 | — | t-Bu | Me | H | Cl | H | H |
| bA133 | bB133 | — | t-Bu | Me | H | H | Cl | H |
| bA134 | bB134 | — | t-Bu | Me | H | H | H | Cl |
| bA135 | bB135 | — | t-Bu | Me | H | H | H | H |
| bA136 | bB136 | — | t-Bu | Me | Et | H | H | H |
| bA137 | bB137 | — | t-Bu | Me | H | Et | H | H |
| bA138 | bB138 | — | t-Bu | Me | H | H | Et | H |
| bA139 | bB139 | — | t-Bu | Me | H | H | H | Et |
| bA140 | bB140 | — | t-Bu | Me | OMe | H | H | H |
| bA141 | bB141 | — | t-Bu | Me | H | OMe | H | H |
| bA142 | bB142 | — | t-Bu | Me | H | H | OMe | H |
| bA143 | bB143 | — | t-Bu | Me | H | H | H | OMe |
| bA144 | bB144 | — | t-Bu | Me | F | H | H | H |
| bA145 | bB145 | — | t-Bu | Me | H | F | H | H |
| bA146 | bB146 | — | t-Bu | Me | H | H | F | H |

TABLE 2-continued

Compounds of the formula (Ib-A) and (Ib-B)

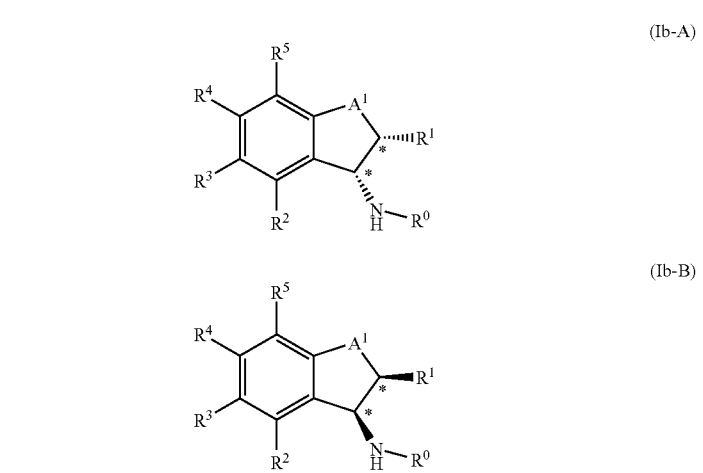

(Ib-A)

(Ib-B)

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA147 | bB147 | — | t-Bu | Me | H | H | H | F |
| bA148 | bB148 | — | Ph | Me | H | H | H | H |
| bA149 | bB149 | — | Ph | Me | Me | H | H | H |
| bA150 | bB150 | — | Ph | Me | Me | Me | H | H |
| bA151 | bB151 | — | Ph | Me | H | H | Me | H |
| bA152 | bB152 | — | Ph | Me | H | H | H | Me |
| bA153 | bB153 | — | Ph | Me | Cl | H | H | H |
| bA154 | bB154 | — | Ph | Me | H | Cl | H | H |
| bA155 | bB155 | — | Ph | Me | H | H | Cl | H |
| bA156 | bB156 | — | Ph | Me | H | H | H | Cl |
| bA157 | bB157 | — | Ph | Me | H | H | H | H |
| bA158 | bB158 | — | Ph | Me | Et | H | H | H |
| bA159 | bB159 | — | Ph | Me | H | Et | H | H |
| bA160 | bB160 | — | Ph | Me | H | H | Et | H |
| bA161 | bB161 | — | Ph | Me | H | H | H | Et |
| bA162 | bB162 | — | Ph | Me | OMe | H | H | H |
| bA163 | bB163 | — | Ph | Me | H | OMe | H | H |
| bA164 | bB164 | — | Ph | Me | H | H | OMe | H |
| bA165 | bB165 | — | Ph | Me | H | H | H | OMe |
| bA166 | bB166 | — | Ph | Me | F | H | H | H |
| bA167 | bB167 | — | Ph | Me | H | F | H | H |
| bA168 | bB168 | — | Ph | Me | H | H | F | H |
| bA169 | bB169 | — | Ph | Me | H | H | H | F |
| bA170 | bB170 | $CH_2$ | Me | Me | H | H | H | H |
| bA171 | bB171 | $CH_2$ | Me | Me | Me | H | H | H |
| bA172 | bB172 | $CH_2$ | Me | Me | H | Me | H | H |
| bA173 | bB173 | $CH_2$ | Me | Me | H | H | Me | H |
| bA174 | bB174 | $CH_2$ | Me | Me | H | H | H | Me |
| bA175 | bB175 | $CH_2$ | Me | Me | Cl | H | H | H |
| bA176 | bB176 | $CH_2$ | Me | Me | H | Cl | H | H |
| bA177 | bB177 | $CH_2$ | Me | Me | H | H | Cl | H |
| bA178 | bB178 | $CH_2$ | Me | Me | H | H | H | Cl |
| bA179 | bB179 | $CH_2$ | Me | Me | Et | H | H | H |
| bA180 | bB180 | $CH_2$ | Me | Me | H | Et | H | H |
| bA181 | bB181 | $CH_2$ | Me | Me | H | H | Et | H |
| bA182 | bB182 | $CH_2$ | Me | Me | H | H | H | Et |
| bA183 | bB183 | $CH_2$ | Me | Me | OMe | H | H | H |
| bA184 | bB184 | $CH_2$ | Me | Me | H | OMe | H | H |
| bA185 | bB185 | $CH_2$ | Me | Me | H | H | OMe | H |
| bA186 | bB186 | $CH_2$ | Me | Me | H | H | H | OMe |
| bA187 | bB187 | $CH_2$ | Me | Me | F | H | H | H |
| bA188 | bB188 | $CH_2$ | Me | Me | H | F | H | H |
| bA189 | bB189 | $CH_2$ | Me | Me | H | H | F | H |
| bA190 | bB190 | $CH_2$ | Me | Me | H | H | H | F |
| bA191 | bB191 | $CH_2$ | Et | Me | H | H | H | H |
| bA192 | bB192 | $CH_2$ | Et | Me | Me | H | H | H |
| bA193 | bB193 | $CH_2$ | Et | Me | H | Me | H | H |
| bA194 | bB194 | $CH_2$ | Et | Me | H | H | Me | H |

TABLE 2-continued

Compounds of the formula (Ib-A) and (Ib-B)

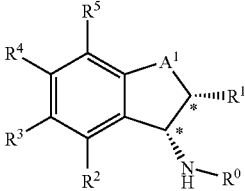
(Ib-A)

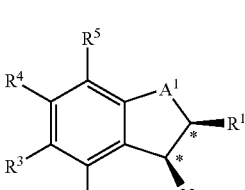
(Ib-B)

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA195 | bB195 | $CH_2$ | Et | Me | H | H | H | Me |
| bA196 | bB196 | $CH_2$ | Et | Me | Cl | H | H | H |
| bA197 | bB197 | $CH_2$ | Et | Me | H | Cl | H | H |
| bA198 | bB198 | $CH_2$ | Et | Me | H | H | Cl | H |
| bA199 | bB199 | $CH_2$ | Et | Me | H | H | H | Cl |
| bA200 | bB200 | $CH_2$ | Et | Me | Et | H | H | H |
| bA201 | bB201 | $CH_2$ | Et | Me | H | Et | H | H |
| bA202 | bB202 | $CH_2$ | Et | Me | H | H | Et | H |
| bA203 | bB203 | $CH_2$ | Et | Me | H | H | H | Et |
| bA204 | bB204 | $CH_2$ | Et | Me | OMe | H | H | H |
| bA205 | bB205 | $CH_2$ | Et | Me | H | OMe | H | H |
| bA206 | bB206 | $CH_2$ | Et | Me | H | H | OMe | H |
| bA207 | bB207 | $CH_2$ | Et | Me | H | H | H | OMe |
| bA208 | bB208 | $CH_2$ | Et | Me | F | H | H | H |
| bA209 | bB209 | $CH_2$ | Et | Me | H | F | H | H |
| bA210 | bB210 | $CH_2$ | Et | Me | H | H | F | H |
| bA211 | bB211 | $CH_2$ | Et | Me | H | H | H | F |
| bA212 | bB212 | $CH_2$ | Allyl | Me | H | H | H | H |
| bA213 | bB213 | $CH_2$ | Allyl | Me | Me | H | H | H |
| bA214 | bB214 | $CH_2$ | Allyl | Me | H | Me | H | H |
| bA215 | bB215 | $CH_2$ | Allyl | Me | H | H | Me | H |
| bA216 | bB216 | $CH_2$ | Allyl | Me | H | H | H | Me |
| bA217 | bB217 | $CH_2$ | Allyl | Allyl | Me | H | H | H |
| bA218 | bB218 | $CH_2$ | Allyl | Allyl | H | Me | H | H |
| bA219 | bB219 | $CH_2$ | Allyl | Allyl | H | H | Me | H |
| bA220 | bB220 | $CH_2$ | Allyl | Allyl | H | H | H | Me |
| bA221 | bB221 | $CH_2$ | Allyl | Me | Cl | H | H | H |
| bA222 | bB222 | $CH_2$ | Allyl | Me | H | Cl | H | H |
| bA223 | bB223 | $CH_2$ | Allyl | Me | H | H | Cl | H |
| bA224 | bB224 | $CH_2$ | Allyl | Me | H | H | H | Cl |
| bA225 | bB225 | $CH_2$ | Allyl | Me | Et | H | H | H |
| bA226 | bB226 | $CH_2$ | Allyl | Me | H | Et | H | H |
| bA227 | bB227 | $CH_2$ | Allyl | Me | H | H | Et | H |
| bA228 | bB228 | $CH_2$ | Allyl | Me | H | H | H | Et |
| bA229 | bB229 | $CH_2$ | Allyl | Me | OMe | H | H | H |
| bA230 | bB230 | $CH_2$ | Allyl | Me | H | OMe | H | H |
| bA231 | bB231 | $CH_2$ | Allyl | Me | H | H | OMe | H |
| bA232 | bB232 | $CH_2$ | Allyl | Me | H | H | H | OMe |
| bA233 | bB233 | $CH_2$ | Allyl | Me | F | H | H | H |
| bA234 | bB234 | $CH_2$ | Allyl | Me | H | F | H | H |
| bA235 | bB235 | $CH_2$ | Allyl | Me | H | H | F | H |
| bA236 | bB236 | $CH_2$ | Allyl | Me | H | H | H | F |
| bA237 | bB237 | $CH_2$ | Bzl | Me | H | H | H | H |
| bA238 | bB238 | $CH_2$ | Bzl | Me | Me | H | H | H |
| bA239 | bB239 | $CH_2$ | Bzl | Me | H | Me | H | H |
| bA240 | bB240 | $CH_2$ | Bzl | Me | H | H | Me | H |
| bA241 | bB241 | $CH_2$ | Bzl | Me | H | H | H | Me |
| bA242 | bB242 | $CH_2$ | Bzl | Me | Cl | H | H | H |

TABLE 2-continued

Compounds of the formula (Ib-A) and (Ib-B)

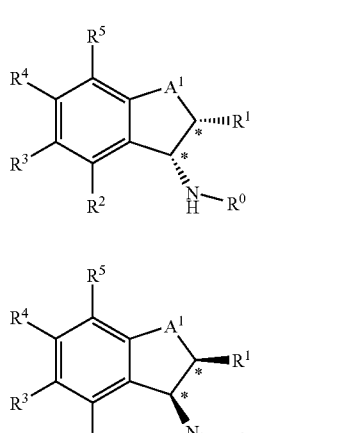
(Ib-A)

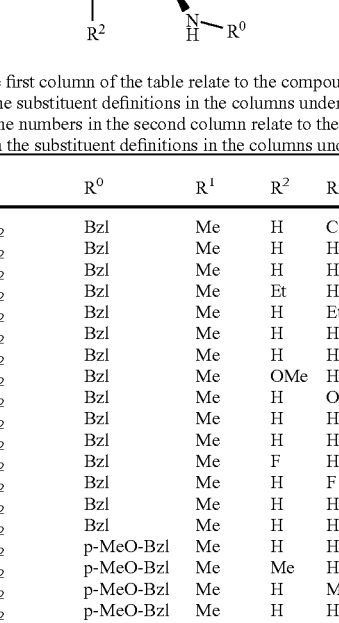
(Ib-B)

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA243 | bB243 | $CH_2$ | Bzl | Me | H | Cl | H | H |
| bA244 | bB244 | $CH_2$ | Bzl | Me | H | H | Cl | H |
| bA245 | bB245 | $CH_2$ | Bzl | Me | H | H | H | Cl |
| bA246 | bB246 | $CH_2$ | Bzl | Me | Et | H | H | H |
| bA247 | bB247 | $CH_2$ | Bzl | Me | H | Et | H | H |
| bA248 | bB248 | $CH_2$ | Bzl | Me | H | H | Et | H |
| bA249 | bB249 | $CH_2$ | Bzl | Me | H | H | H | Et |
| bA250 | bB250 | $CH_2$ | Bzl | Me | OMe | H | H | H |
| bA251 | bB251 | $CH_2$ | Bzl | Me | H | OMe | H | H |
| bA252 | bB252 | $CH_2$ | Bzl | Me | H | H | OMe | H |
| bA253 | bB253 | $CH_2$ | Bzl | Me | H | H | H | OMe |
| bA254 | bB254 | $CH_2$ | Bzl | Me | F | H | H | H |
| bA255 | bB255 | $CH_2$ | Bzl | Me | H | F | H | H |
| bA256 | bB256 | $CH_2$ | Bzl | Me | H | H | F | H |
| bA257 | bB257 | $CH_2$ | Bzl | Me | H | H | H | F |
| bA258 | bB258 | $CH_2$ | p-MeO-Bzl | Me | H | H | H | H |
| bA259 | bB259 | $CH_2$ | p-MeO-Bzl | Me | Me | H | H | H |
| bA260 | bB260 | $CH_2$ | p-MeO-Bzl | Me | H | Me | H | H |
| bA261 | bB261 | $CH_2$ | p-MeO-Bzl | Me | H | H | Me | H |
| bA262 | bB262 | $CH_2$ | p-MeO-Bzl | Me | H | H | H | Me |
| bA263 | bB263 | $CH_2$ | p-MeO-Bzl | Me | Cl | H | H | H |
| bA264 | bB264 | $CH_2$ | p-MeO-Bzl | Me | H | Cl | H | H |
| bA265 | bB265 | $CH_2$ | p-MeO-Bzl | Me | H | H | Cl | H |
| bA266 | bB266 | $CH_2$ | p-MeO-Bzl | Me | H | H | H | Cl |
| bA267 | bB267 | $CH_2$ | p-MeO-Bzl | Me | Et | H | H | H |
| bA268 | bB268 | $CH_2$ | p-MeO-Bzl | Me | H | Et | H | H |
| bA269 | bB269 | $CH_2$ | p-MeO-Bzl | Me | H | H | Et | H |
| bA270 | bB270 | $CH_2$ | p-MeO-Bzl | Me | H | H | H | Et |
| bA271 | bB271 | $CH_2$ | p-MeO-Bzl | Me | OMe | H | H | H |
| bA272 | bB272 | $CH_2$ | p-MeO-Bzl | Me | H | OMe | H | H |
| bA273 | bB273 | $CH_2$ | p-MeO-Bzl | Me | H | H | OMe | H |
| bA274 | bB274 | $CH_2$ | p-MeO-Bzl | Me | H | H | H | OMe |
| bA275 | bB275 | $CH_2$ | p-MeO-Bzl | Me | F | H | H | H |
| bA276 | bB276 | $CH_2$ | p-MeO-Bzl | Me | H | F | H | H |
| bA277 | bB277 | $CH_2$ | p-MeO-Bzl | Me | H | H | F | H |
| bA278 | bB278 | $CH_2$ | p-MeO-Bzl | Me | H | H | H | F |
| bA279 | bB279 | $CH_2$ | i-Pr | Me | Me | H | H | H |
| bA280 | bB280 | $CH_2$ | i-Pr | Me | H | Me | H | H |
| bA281 | bB281 | $CH_2$ | i-Pr | Me | H | H | Me | H |
| bA282 | bB282 | $CH_2$ | i-Pr | Me | H | H | H | Me |
| bA283 | bB283 | $CH_2$ | i-Pr | Me | Cl | H | H | H |
| bA284 | bB284 | $CH_2$ | i-Pr | Me | H | Cl | H | H |
| bA285 | bB285 | $CH_2$ | i-Pr | Me | H | H | Cl | H |
| bA286 | bB286 | $CH_2$ | i-Pr | Me | H | H | H | Cl |
| bA287 | bB287 | $CH_2$ | i-Pr | Me | Et | H | H | H |
| bA288 | bB288 | $CH_2$ | i-Pr | Me | H | Et | H | H |
| bA289 | bB289 | $CH_2$ | i-Pr | Me | H | H | Et | H |
| bA290 | bB290 | $CH_2$ | i-Pr | Me | H | H | H | Et |

TABLE 2-continued

Compounds of the formula (Ib-A) and (Ib-B)

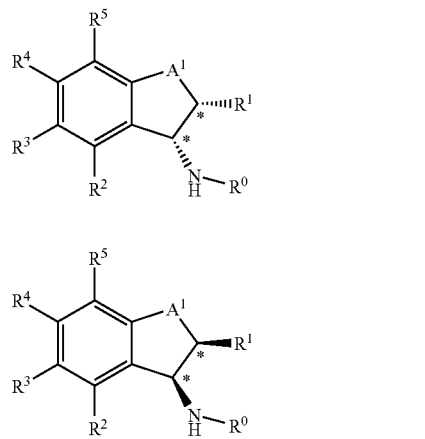

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA291 | bB291 | $CH_2$ | i-Pr | Me | OMe | H | H | H |
| bA292 | bB292 | $CH_2$ | i-Pr | Me | H | OMe | H | H |
| bA293 | bB293 | $CH_2$ | i-Pr | Me | H | H | OMe | H |
| bA294 | bB294 | $CH_2$ | i-Pr | Me | H | H | H | OMe |
| bA295 | bB295 | $CH_2$ | i-Pr | Me | F | H | H | H |
| bA296 | bB296 | $CH_2$ | i-Pr | Me | H | F | H | H |
| bA297 | bB297 | $CH_2$ | i-Pr | Me | H | H | F | H |
| bA298 | bB298 | $CH_2$ | i-Pr | Me | H | H | H | F |
| bA299 | bB299 | $CH_2$ | t-Bu | Me | H | H | H | H |
| bA300 | bB300 | $CH_2$ | t-Bu | Me | Me | H | H | H |
| bA301 | bB301 | $CH_2$ | t-Bu | Me | M | Me | H | H |
| bA302 | bB302 | $CH_2$ | t-Bu | Me | H | H | Me | H |
| bA303 | bB303 | $CH_2$ | t-Bu | Me | H | H | H | Me |
| bA304 | bB304 | $CH_2$ | t-Bu | Me | Cl | H | H | H |
| bA305 | bB305 | $CH_2$ | t-Bu | Me | H | Cl | H | H |
| bA306 | bB306 | $CH_2$ | t-Bu | Me | H | H | Cl | H |
| bA307 | bB307 | $CH_2$ | t-Bu | Me | H | H | H | Cl |
| bA308 | bB308 | $CH_2$ | t-Bu | Me | H | H | H | H |
| bA309 | bB309 | $CH_2$ | t-Bu | Me | Et | H | H | H |
| bA310 | bB310 | $CH_2$ | t-Bu | Me | H | Et | H | H |
| bA311 | bB311 | $CH_2$ | t-Bu | Me | H | H | Et | H |
| bA312 | bB312 | $CH_2$ | t-Bu | Me | H | H | H | Et |
| bA313 | bB313 | $CH_2$ | t-Bu | Me | OMe | H | H | H |
| bA314 | bB314 | $CH_2$ | t-Bu | Me | H | OMe | H | H |
| bA315 | bB315 | $CH_2$ | t-Bu | Me | H | H | OMe | H |
| bA316 | bB316 | $CH_2$ | t-Bu | Me | H | H | H | OMe |
| bA317 | bB317 | $CH_2$ | t-Bu | Me | F | H | H | H |
| bA318 | bB318 | $CH_2$ | t-Bu | Me | H | F | H | H |
| bA319 | bB319 | $CH_2$ | t-Bu | Me | H | H | F | H |
| bA320 | bB320 | $CH_2$ | t-Bu | Me | H | H | H | F |
| bA321 | bB321 | $CH_2$ | Ph | Me | H | H | H | H |
| bA322 | bB322 | $CH_2$ | Ph | Me | Me | H | H | H |
| bA323 | bB323 | $CH_2$ | Ph | Me | Me | Me | H | H |
| bA324 | bB324 | $CH_2$ | Ph | Me | H | H | Me | H |
| bA325 | bB325 | $CH_2$ | Ph | Me | H | H | H | Me |
| bA326 | bB326 | $CH_2$ | Ph | Me | Cl | H | H | H |
| bA327 | bB327 | $CH_2$ | Ph | Me | H | Cl | H | H |
| bA328 | bB328 | $CH_2$ | Ph | Me | H | H | Cl | H |
| bA329 | bB329 | $CH_2$ | Ph | Me | H | H | H | Cl |
| bA330 | bB330 | $CH_2$ | Ph | Me | H | H | H | H |
| bA331 | bB331 | $CH_2$ | Ph | Me | Et | H | H | H |
| bA332 | bB332 | $CH_2$ | Ph | Me | H | Et | H | H |
| bA333 | bB333 | $CH_2$ | Ph | Me | H | H | Et | H |
| bA334 | bB334 | $CH_2$ | Ph | Me | H | H | H | Et |
| bA335 | bB335 | $CH_2$ | Ph | Me | OMe | H | H | H |
| bA336 | bB336 | $CH_2$ | Ph | Me | H | OMe | H | H |
| bA337 | bB337 | $CH_2$ | Ph | Me | H | H | OMe | H |
| bA338 | bB338 | $CH_2$ | Ph | Me | H | H | H | OMe |

TABLE 2-continued

Compounds of the formula (Ib-A) and (Ib-B)

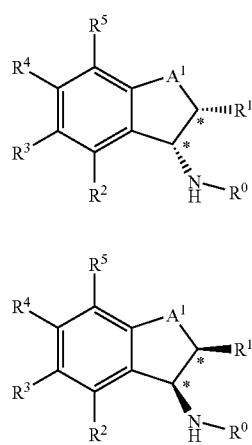
(Ib-A)

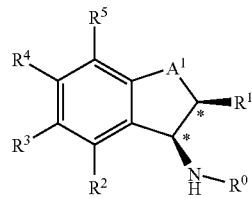
(Ib-B)

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA339 | bB339 | $CH_2$ | Ph | Me | F | H | H | H |
| bA340 | bB340 | $CH_2$ | Ph | Me | H | F | H | H |
| bA341 | bB341 | $CH_2$ | Ph | Me | H | H | F | H |
| bA342 | bB342 | $CH_2$ | Ph | Me | H | H | H | F |
| bA343 | bB343 | $CH_2CH_2$ | Me | Me | H | H | H | H |
| bA344 | bB344 | $CH_2CH_2$ | Me | Me | Me | H | H | H |
| bA345 | bB345 | $CH_2CH_2$ | Me | Me | H | Me | H | H |
| bA346 | bB346 | $CH_2CH_2$ | Me | Me | H | H | Me | H |
| bA347 | bB347 | $CH_2CH_2$ | Me | Me | H | H | H | Me |
| bA348 | bB348 | $CH_2CH_2$ | Me | Me | Cl | H | H | H |
| bA349 | bB349 | $CH_2CH_2$ | Me | Me | H | Cl | H | H |
| bA350 | bB350 | $CH_2CH_2$ | Me | Me | H | H | Cl | H |
| bA351 | bB351 | $CH_2CH_2$ | Me | Me | H | H | H | Cl |
| bA352 | bB352 | $CH_2CH_2$ | Me | Me | Et | H | H | H |
| bA353 | bB353 | $CH_2CH_2$ | Me | Me | H | Et | H | H |
| bA354 | bB354 | $CH_2CH_2$ | Me | Me | H | H | Et | H |
| bA355 | bB355 | $CH_2CH_2$ | Me | Me | H | H | H | Et |
| bA356 | bB356 | $CH_2CH_2$ | Me | Me | OMe | H | H | H |
| bA357 | bB357 | $CH_2CH_2$ | Me | Me | H | OMe | H | H |
| bA358 | bB358 | $CH_2CH_2$ | Me | Me | H | H | OMe | H |
| bA359 | bB359 | $CH_2CH_2$ | Me | Me | H | H | H | OMe |
| bA360 | bB360 | $CH_2CH_2$ | Me | Me | F | H | H | H |
| bA361 | bB361 | $CH_2CH_2$ | Me | Me | H | F | H | H |
| bA362 | bB362 | $CH_2CH_2$ | Me | Me | H | H | F | H |
| bA363 | bB363 | $CH_2CH_2$ | Me | Me | H | H | H | F |
| bA364 | bB364 | $CH_2CH_2$ | Et | Me | H | H | H | H |
| bA365 | bB365 | $CH_2CH_2$ | Et | Me | Me | H | H | H |
| bA366 | bB366 | $CH_2CH_2$ | Et | Me | H | Me | H | H |
| bA367 | bB367 | $CH_2CH_2$ | Et | Me | H | H | Me | H |
| bA368 | bB368 | $CH_2CH_2$ | Et | Me | H | H | H | Me |
| bA369 | bB369 | $CH_2CH_2$ | Et | Me | Cl | H | H | H |
| bA370 | bB370 | $CH_2CH_2$ | Et | Me | H | Cl | H | H |
| bA371 | bB371 | $CH_2CH_2$ | Et | Me | H | H | Cl | H |
| bA372 | bB372 | $CH_2CH_2$ | Et | Me | H | H | H | Cl |
| bA373 | bB373 | $CH_2CH_2$ | Et | Me | Et | H | H | H |
| bA374 | bB374 | $CH_2CH_2$ | Et | Me | H | Et | H | H |
| bA375 | bB375 | $CH_2CH_2$ | Et | Me | H | H | Et | H |
| bA376 | bB376 | $CH_2CH_2$ | Et | Me | H | H | H | Et |
| bA377 | bB377 | $CH_2CH_2$ | Et | Me | OMe | H | H | H |
| bA378 | bB378 | $CH_2CH_2$ | Et | Me | H | OMe | H | H |
| bA379 | bB379 | $CH_2CH_2$ | Et | Me | H | H | OMe | H |
| bA380 | bB380 | $CH_2CH_2$ | Et | Me | H | H | H | OMe |
| bA381 | bB381 | $CH_2CH_2$ | Et | Me | F | H | H | H |
| bA382 | bB382 | $CH_2CH_2$ | Et | Me | H | F | H | H |
| bA383 | bB383 | $CH_2CH_2$ | Et | Me | H | H | F | H |
| bA384 | bB384 | $CH_2CH_2$ | Et | Me | H | H | H | F |
| bA385 | bB385 | $CH_2CH_2$ | Allyl | Me | H | H | H | H |
| bA386 | bB386 | $CH_2CH_2$ | Allyl | Me | Me | H | H | H |

TABLE 2-continued

Compounds of the formula (Ib-A) and (Ib-B)

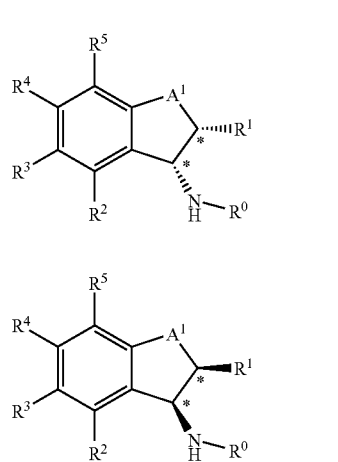
(Ib-A)

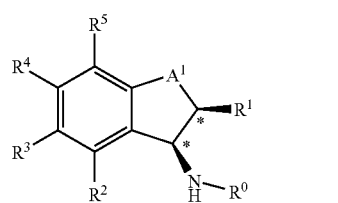
(Ib-B)

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA387 | bB387 | $CH_2CH_2$ | Allyl | Me | H | Me | H | H |
| bA388 | bB388 | $CH_2CH_2$ | Allyl | Me | H | H | Me | H |
| bA389 | bB389 | $CH_2CH_2$ | Allyl | Me | H | H | H | Me |
| bA390 | bB390 | $CH_2CH_2$ | Allyl | Me | Cl | H | H | H |
| bA391 | bB391 | $CH_2CH_2$ | Allyl | Me | H | Cl | H | H |
| bA392 | bB392 | $CH_2CH_2$ | Allyl | Me | H | H | Cl | H |
| bA393 | bB393 | $CH_2CH_2$ | Allyl | Me | H | H | H | Cl |
| bA394 | bB394 | $CH_2CH_2$ | Allyl | Me | Et | H | H | H |
| bA395 | bB395 | $CH_2CH_2$ | Allyl | Me | H | Et | H | H |
| bA396 | bB396 | $CH_2CH_2$ | Allyl | Me | H | H | Et | H |
| bA397 | bB397 | $CH_2CH_2$ | Allyl | Me | H | H | H | Et |
| bA398 | bB398 | $CH_2CH_2$ | Allyl | Me | OMe | H | H | H |
| bA399 | bB399 | $CH_2CH_2$ | Allyl | Me | H | OMe | H | H |
| bA400 | bB400 | $CH_2CH_2$ | Allyl | Me | H | H | OMe | H |
| bA401 | bB401 | $CH_2CH_2$ | Allyl | Me | H | H | H | OMe |
| bA402 | bB402 | $CH_2CH_2$ | Allyl | Me | F | H | H | H |
| bA403 | bB403 | $CH_2CH_2$ | Allyl | Me | H | F | H | H |
| bA404 | bB404 | $CH_2CH_2$ | Allyl | Me | H | H | F | H |
| bA405 | bB405 | $CH_2CH_2$ | Allyl | Me | H | H | H | F |
| bA406 | bB406 | $CH_2CH_2$ | Bzl | Me | H | H | H | H |
| bA407 | bB407 | $CH_2CH_2$ | Bzl | Me | Me | H | H | H |
| bA408 | bB408 | $CH_2CH_2$ | Bzl | Me | H | Me | H | H |
| bA409 | bB409 | $CH_2CH_2$ | Bzl | Me | H | H | Me | H |
| bA410 | bB410 | $CH_2CH_2$ | Bzl | Me | H | H | H | Me |
| bA411 | bB411 | $CH_2CH_2$ | Bzl | Me | Cl | H | H | H |
| bA412 | bB412 | $CH_2CH_2$ | Bzl | Me | H | Cl | H | H |
| bA413 | bB413 | $CH_2CH_2$ | Bzl | Me | H | H | Cl | H |
| bA414 | bB414 | $CH_2CH_2$ | Bzl | Me | H | H | H | Cl |
| bA415 | bB415 | $CH_2CH_2$ | Bzl | Me | Et | H | H | H |
| bA416 | bB416 | $CH_2CH_2$ | Bzl | Me | H | Et | H | H |
| bA417 | bB417 | $CH_2CH_2$ | Bzl | Me | H | H | Et | H |
| bA418 | bB418 | $CH_2CH_2$ | Bzl | Me | H | H | H | Et |
| bA419 | bB419 | $CH_2CH_2$ | Bzl | Me | OMe | H | H | H |
| bA420 | bB420 | $CH_2CH_2$ | Bzl | Me | H | OMe | H | H |
| bA421 | bB421 | $CH_2CH_2$ | Bzl | Me | H | H | OMe | H |
| bA422 | bB422 | $CH_2CH_2$ | Bzl | Me | H | H | H | OMe |
| bA423 | bB423 | $CH_2CH_2$ | Bzl | Me | F | H | H | H |
| bA424 | bB424 | $CH_2CH_2$ | Bzl | Me | H | F | H | H |
| bA425 | bB425 | $CH_2CH_2$ | Bzl | Me | H | H | F | H |
| bA426 | bB426 | $CH_2CH_2$ | Bzl | Me | H | H | H | F |
| bA427 | bB427 | $CH_2CH_2$ | p-MeO-Bzl | Me | H | H | H | H |
| bA428 | bB428 | $CH_2CH_2$ | p-MeO-Bzl | Me | Me | H | H | H |
| bA429 | bB429 | $CH_2CH_2$ | p-MeO-Bzl | Me | H | Me | H | H |
| bA430 | bB430 | $CH_2CH_2$ | p-MeO-Bzl | Me | H | H | Me | H |
| bA431 | bB431 | $CH_2CH_2$ | p-MeO-Bzl | Me | H | H | H | Me |
| bA432 | bB432 | $CH_2CH_2$ | p-MeO-Bzl | Me | Cl | H | H | H |
| bA433 | bB433 | $CH_2CH_2$ | p-MeO-Bzl | Me | H | Cl | H | H |
| bA434 | bB434 | $CH_2CH_2$ | p-MeO-Bzl | Me | H | H | Cl | H |

TABLE 2-continued

Compounds of the formula (Ib-A) and (Ib-B)

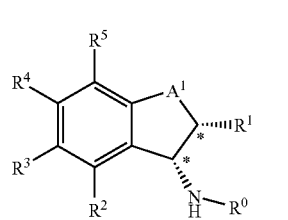
(Ib-A)

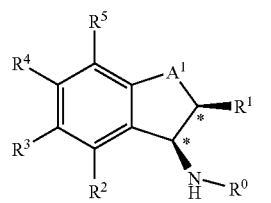
(Ib-B)

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA435 | bB435 | $CH_2CH_2$ | p-MeO-Bzl | Me | H | H | H | Cl |
| bA436 | bB436 | $CH_2CH_2$ | p-MeO-Bzl | Me | Et | H | H | H |
| bA437 | bB437 | $CH_2CH_2$ | p-MeO-Bzl | Me | H | Et | H | H |
| bA438 | bB438 | $CH_2CH_2$ | p-MeO-Bzl | Me | H | H | Et | H |
| bA439 | bB439 | $CH_2CH_2$ | p-MeO-Bzl | Me | H | H | H | Et |
| bA440 | bB440 | $CH_2CH_2$ | p-MeO-Bzl | Me | OMe | H | H | H |
| bA441 | bB441 | $CH_2CH_2$ | p-MeO-Bzl | Me | H | OMe | H | H |
| bA442 | bB442 | $CH_2CH_2$ | p-MeO-Bzl | Me | H | H | OMe | H |
| bA443 | bB443 | $CH_2CH_2$ | p-MeO-Bzl | Me | H | H | H | OMe |
| bA444 | bB444 | $CH_2CH_2$ | p-MeO-Bzl | Me | F | H | H | H |
| bA445 | bB445 | $CH_2CH_2$ | p-MeO-Bzl | Me | H | F | H | H |
| bA446 | bB446 | $CH_2CH_2$ | p-MeO-Bzl | Me | H | H | F | H |
| bA447 | bB447 | $CH_2CH_2$ | p-MeO-Bzl | Me | H | H | H | F |
| bA448 | bB448 | $CH_2CH_2$ | i-Pr | Me | Me | H | H | F |
| bA449 | bB449 | $CH_2CH_2$ | i-Pr | Me | H | Me | H | H |
| bA450 | bB450 | $CH_2CH_2$ | i-Pr | Me | H | H | Me | H |
| bA451 | bB451 | $CH_2CH_2$ | i-Pr | Me | H | H | H | Me |
| bA452 | bB452 | $CH_2CH_2$ | i-Pr | Me | Cl | H | H | H |
| bA453 | bB453 | $CH_2CH_2$ | i-Pr | Me | H | Cl | H | H |
| bA454 | bB454 | $CH_2CH_2$ | i-Pr | Me | H | H | Cl | H |
| bA455 | bB455 | $CH_2CH_2$ | i-Pr | Me | H | H | H | Cl |
| bA456 | bB456 | $CH_2CH_2$ | i-Pr | Me | Et | H | H | H |
| bA457 | bB457 | $CH_2CH_2$ | i-Pr | Me | H | Et | H | H |
| bA458 | bB458 | $CH_2CH_2$ | i-Pr | Me | H | H | Et | H |
| bA459 | bB459 | $CH_2CH_2$ | i-Pr | Me | H | H | H | Et |
| bA460 | bB460 | $CH_2CH_2$ | i-Pr | Me | OMe | H | H | H |
| bA461 | bB461 | $CH_2CH_2$ | i-Pr | Me | H | OMe | H | H |
| bA462 | bB462 | $CH_2CH_2$ | i-Pr | Me | H | H | OMe | H |
| bA463 | bB463 | $CH_2CH_2$ | i-Pr | Me | H | H | H | OMe |
| bA464 | bB464 | $CH_2CH_2$ | i-Pr | Me | F | H | H | H |
| bA465 | bB465 | $CH_2CH_2$ | i-Pr | Me | H | F | H | H |
| bA466 | bB466 | $CH_2CH_2$ | i-Pr | Me | H | H | F | H |
| bA467 | bB467 | $CH_2CH_2$ | i-Pr | Me | H | H | H | F |
| bA468 | bB468 | $CH_2CH_2$ | t-Bu | Me | H | H | H | H |
| bA469 | bB469 | $CH_2CH_2$ | t-Bu | Me | Me | H | H | H |
| bA470 | bB470 | $CH_2CH_2$ | t-Bu | Me | Me | Me | H | H |
| bA471 | bB471 | $CH_2CH_2$ | t-Bu | Me | H | H | Me | H |
| bA472 | bB472 | $CH_2CH_2$ | t-Bu | Me | H | H | H | Me |
| bA473 | bB473 | $CH_2CH_2$ | t-Bu | Me | Cl | H | H | H |
| bA474 | bB474 | $CH_2CH_2$ | t-Bu | Me | H | Cl | H | H |
| bA475 | bB475 | $CH_2CH_2$ | t-Bu | Me | H | H | Cl | H |
| bA476 | bB476 | $CH_2CH_2$ | t-Bu | Me | H | H | H | Cl |
| bA477 | bB477 | $CH_2CH_2$ | t-Bu | Me | H | H | H | H |
| bA478 | bB478 | $CH_2CH_2$ | t-Bu | Me | Et | H | H | H |
| bA479 | bB479 | $CH_2CH_2$ | t-Bu | Me | H | Et | H | H |
| bA480 | bB480 | $CH_2CH_2$ | t-Bu | Me | H | H | Et | H |
| bA481 | bB481 | $CH_2CH_2$ | t-Bu | Me | H | H | H | Et |
| bA482 | bB482 | $CH_2CH_2$ | t-Bu | Me | OMe | H | H | H |

TABLE 2-continued

Compounds of the formula (Ib-A) and (Ib-B)

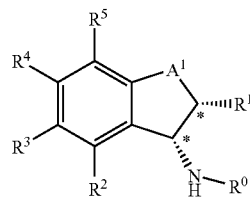
(Ib-A)

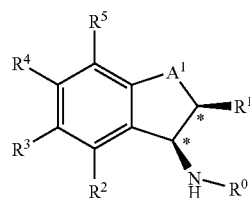
(Ib-B)

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA483 | bB483 | CH$_2$CH$_2$ | t-Bu | Me | H | OMe | H | H |
| bA484 | bB484 | CH$_2$CH$_2$ | t-Bu | Me | H | H | OMe | H |
| bA485 | bB485 | CH$_2$CH$_2$ | t-Bu | Me | H | H | H | OMe |
| bA486 | bB486 | CH$_2$CH$_2$ | t-Bu | Me | F | H | H | H |
| bA487 | bB487 | CH$_2$CH$_2$ | t-Bu | Me | H | F | H | H |
| bA488 | bB488 | CH$_2$CH$_2$ | t-Bu | Me | H | H | F | H |
| bA489 | bB489 | CH$_2$CH$_2$ | t-Bu | Me | H | H | H | F |
| bA490 | bB490 | CH$_2$CH$_2$ | Ph | Me | H | H | H | H |
| bA491 | bB491 | CH$_2$CH$_2$ | Ph | Me | Me | H | H | H |
| bA492 | bB492 | CH$_2$CH$_2$ | Ph | Me | Me | Me | H | H |
| bA493 | bB493 | CH$_2$CH$_2$ | Ph | Me | H | H | Me | H |
| bA494 | bB494 | CH$_2$CH$_2$ | Ph | Me | H | H | H | Me |
| bA495 | bB495 | CH$_2$CH$_2$ | Ph | Me | Cl | H | H | H |
| bA496 | bB496 | CH$_2$CH$_2$ | Ph | Me | H | Cl | H | H |
| bA497 | bB497 | CH$_2$CH$_2$ | Ph | Me | H | H | Cl | H |
| bA498 | bB498 | CH$_2$CH$_2$ | Ph | Me | H | H | H | Cl |
| bA499 | bB499 | CH$_2$CH$_2$ | Ph | Me | H | H | H | H |
| bA500 | bB500 | CH$_2$CH$_2$ | Ph | Me | Et | H | H | H |
| bA501 | bB501 | CH$_2$CH$_2$ | Ph | Me | H | Et | H | H |
| bA502 | bB502 | CH$_2$CH$_2$ | Ph | Me | H | H | Et | H |
| bA503 | bB503 | CH$_2$CH$_2$ | Ph | Me | H | H | H | Et |
| bA504 | bB504 | CH$_2$CH$_2$ | Ph | Me | OMe | H | H | H |
| bA505 | bB505 | CH$_2$CH$_2$ | Ph | Me | H | OMe | H | H |
| bA506 | bB506 | CH$_2$CH$_2$ | Ph | Me | H | H | OMe | H |
| bA507 | bB507 | CH$_2$CH$_2$ | Ph | Me | H | H | H | OMe |
| bA508 | bB508 | CH$_2$CH$_2$ | Ph | Me | F | H | H | H |
| bA509 | bB509 | CH$_2$CH$_2$ | Ph | Me | H | F | H | H |
| bA510 | bB510 | CH$_2$CH$_2$ | Ph | Me | H | H | F | H |
| bA511 | bB511 | CH$_2$CH$_2$ | Ph | Me | H | H | H | F |
| bA512 | bB512 | OCH$_2$ | Me | Me | H | H | H | H |
| bA513 | bB513 | OCH$_2$ | Me | Me | Me | H | H | H |
| bA514 | bB514 | OCH$_2$ | Me | Me | H | Me | H | H |
| bA515 | bB515 | OCH$_2$ | Me | Me | H | H | Me | H |
| bA516 | bB516 | OCH$_2$ | Me | Me | H | H | H | Me |
| bA517 | bB517 | OCH$_2$ | Me | Me | Cl | H | H | H |
| bA518 | bB518 | OCH$_2$ | Me | Me | H | Cl | H | H |
| bA519 | bB519 | OCH$_2$ | Me | Me | H | H | Cl | H |
| bA520 | bB520 | OCH$_2$ | Me | Me | H | H | H | Cl |
| bA521 | bB521 | OCH$_2$ | Me | Me | Et | H | H | H |
| bA522 | bB522 | OCH$_2$ | Me | Me | H | Et | H | H |
| bA523 | bB523 | OCH$_2$ | Me | Me | H | H | Et | H |
| bA524 | bB524 | OCH$_2$ | Me | Me | H | H | H | Et |
| bA525 | bB525 | OCH$_2$ | Me | Me | OMe | H | H | H |
| bA526 | bB526 | OCH$_2$ | Me | Me | H | OMe | H | H |
| bA527 | bB527 | OCH$_2$ | Me | Me | H | H | OMe | H |
| bA528 | bB528 | OCH$_2$ | Me | Me | H | H | H | OMe |
| bA529 | bB529 | OCH$_2$ | Me | Me | F | H | H | H |
| bA530 | bB530 | OCH$_2$ | Me | Me | H | F | H | H |

TABLE 2-continued

Compounds of the formula (Ib-A) and (Ib-B)

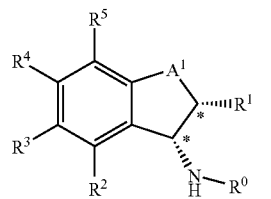
(Ib-A)

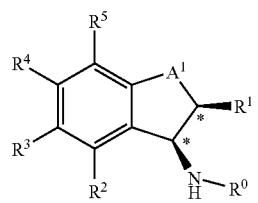
(Ib-B)

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA531 | bB531 | OCH$_2$ | Me | Me | H | H | F | H |
| bA532 | bB532 | OCH$_2$ | Me | Me | H | H | H | F |
| bA533 | bB533 | OCH$_2$ | Et | Me | H | H | H | H |
| bA534 | bB534 | OCH$_2$ | Et | Me | Me | H | H | H |
| bA535 | bB535 | OCH$_2$ | Et | Me | H | Me | H | H |
| bA536 | bB536 | OCH$_2$ | Et | Me | H | H | Me | H |
| bA537 | bB537 | OCH$_2$ | Et | Me | H | H | H | Me |
| bA538 | bB538 | OCH$_2$ | Et | Me | Cl | H | H | H |
| bA539 | bB539 | OCH$_2$ | Et | Me | H | Cl | H | H |
| bA540 | bB540 | OCH$_2$ | Et | Me | H | H | Cl | H |
| bA541 | bB541 | OCH$_2$ | Et | Me | H | H | H | Cl |
| bA542 | bB542 | OCH$_2$ | Et | Me | Et | H | H | H |
| bA543 | bB543 | OCH$_2$ | Et | Me | H | Et | H | H |
| bA544 | bB544 | OCH$_2$ | Et | Me | H | H | Et | H |
| bA545 | bB545 | OCH$_2$ | Et | Me | H | H | H | Et |
| bA546 | bB546 | OCH$_2$ | Et | Me | OMe | H | H | H |
| bA547 | bB547 | OCH$_2$ | Et | Me | H | OMe | H | H |
| bA548 | bB548 | OCH$_2$ | Et | Me | H | H | OMe | H |
| bA549 | bB549 | OCH$_2$ | Et | Me | H | H | H | OMe |
| bA550 | bB550 | OCH$_2$ | Et | Me | F | H | H | H |
| bA551 | bB551 | OCH$_2$ | Et | Me | H | F | H | H |
| bA552 | bB552 | OCH$_2$ | Et | Me | H | H | F | H |
| bA553 | bB553 | OCH$_2$ | Et | Me | H | H | H | F |
| bA554 | bB554 | OCH$_2$ | Allyl | Me | H | H | H | H |
| bA555 | bB555 | OCH$_2$ | Allyl | Me | Me | H | H | H |
| bA556 | bB556 | OCH$_2$ | Allyl | Me | H | Me | H | H |
| bA557 | bB557 | OCH$_2$ | Allyl | Me | H | H | Me | H |
| bA558 | bB558 | OCH$_2$ | Allyl | Me | H | H | H | Me |
| bA559 | bB559 | OCH$_2$ | Allyl | Me | Cl | H | H | H |
| bA560 | bB560 | OCH$_2$ | Allyl | Me | H | Cl | H | H |
| bA561 | bB561 | OCH$_2$ | Allyl | Me | H | H | Cl | H |
| bA562 | bB562 | OCH$_2$ | Allyl | Me | H | H | H | Cl |
| bA563 | bB563 | OCH$_2$ | Allyl | Me | Et | H | H | H |
| bA564 | bB564 | OCH$_2$ | Allyl | Me | H | Et | H | H |
| bA565 | bB565 | OCH$_2$ | Allyl | Me | H | H | Et | H |
| bA566 | bB566 | OCH$_2$ | Allyl | Me | H | H | H | Et |
| bA567 | bB567 | OCH$_2$ | Allyl | Me | OMe | H | H | H |
| bA568 | bB568 | OCH$_2$ | Allyl | Me | H | OMe | H | H |
| bA569 | bB569 | OCH$_2$ | Allyl | Me | H | H | OMe | H |
| bA570 | bB570 | OCH$_2$ | Allyl | Me | H | H | H | OMe |
| bA571 | bB571 | OCH$_2$ | Allyl | Me | F | H | H | H |
| bA572 | bB572 | OCH$_2$ | Allyl | Me | H | F | H | H |
| bA573 | bB573 | OCH$_2$ | Allyl | Me | H | H | F | H |
| bA574 | bB574 | OCH$_2$ | Allyl | Me | H | H | H | F |
| bA575 | bB575 | OCH$_2$ | Bzl | Me | H | H | H | H |
| bA576 | bB576 | OCH$_2$ | Bzl | Me | Me | H | H | H |
| bA577 | bB577 | OCH$_2$ | Bzl | Me | H | Me | H | H |
| bA578 | bB578 | OCH$_2$ | Bzl | Me | H | H | Me | H |

TABLE 2-continued

Compounds of the formula (Ib-A) and (Ib-B)

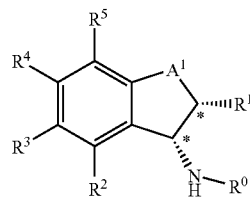
(Ib-A)

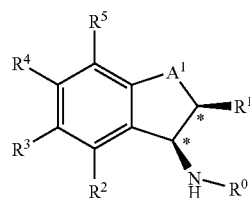
(Ib-B)

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA579 | bB579 | $OCH_2$ | Bzl | Me | H | H | H | Me |
| bA580 | bB580 | $OCH_2$ | Bzl | Me | Cl | H | H | H |
| bA581 | bB581 | $OCH_2$ | Bzl | Me | H | Cl | H | H |
| bA582 | bB582 | $OCH_2$ | Bzl | Me | H | H | Ci | H |
| bA583 | bB583 | $OCH_2$ | Bzl | Me | H | H | H | Cl |
| bA584 | bB584 | $OCH_2$ | Bzl | Me | Et | H | H | H |
| bA585 | bB585 | $OCH_2$ | Bzl | Me | H | Et | H | H |
| bA586 | bB586 | $OCH_2$ | Bzl | Me | H | H | Et | H |
| bA587 | bB587 | $OCH_2$ | Bzl | Me | H | H | H | Et |
| bA588 | bB588 | $OCH_2$ | Bzl | Me | OMe | H | H | H |
| bA589 | bB589 | $OCH_2$ | Bzl | Me | H | OMe | H | H |
| bA590 | bB590 | $OCH_2$ | Bzl | Me | H | H | OMe | H |
| bA591 | bB591 | $OCH_2$ | Bzl | Me | H | H | H | OMe |
| bA592 | bB592 | $OCH_2$ | Bzl | Me | F | H | H | H |
| bA593 | bB593 | $OCH_2$ | Bzl | Me | H | F | H | H |
| bA594 | bB594 | $OCH_2$ | Bzl | Me | H | H | F | H |
| bA595 | bB595 | $OCH_2$ | Bzl | Me | H | H | H | F |
| bA596 | bB596 | $OCH_2$ | p-MeO-Bzl | Me | H | H | H | H |
| bA597 | bB597 | $OCH_2$ | p-MeO-Bzl | Me | Me | H | H | H |
| bA598 | bB598 | $OCH_2$ | p-MeO-Bzl | Me | H | Me | H | H |
| bA599 | bB599 | $OCH_2$ | p-MeO-Bzl | Me | H | H | Me | H |
| bA600 | bB600 | $OCH_2$ | p-MeO-Bzl | Me | H | H | H | Me |
| bA601 | bB601 | $OCH_2$ | p-MeO-Bzl | Me | Cl | H | H | H |
| bA602 | bB602 | $OCH_2$ | p-MeO-Bzl | Me | H | Cl | H | H |
| bA603 | bB603 | $OCH_2$ | p-MeO-Bzl | Me | H | H | Cl | H |
| bA604 | bB604 | $OCH_2$ | p-MeO-Bzl | Me | H | H | H | Cl |
| bA605 | bB605 | $OCH_2$ | p-MeO-Bzl | Me | Et | H | H | H |
| bA606 | bB606 | $OCH_2$ | p-MeO-Bzl | Me | H | Et | H | H |
| bA607 | bB607 | $OCH_2$ | p-MeO-Bzl | Me | H | H | Et | H |
| bA608 | bB608 | $OCH_2$ | p-MeO-Bzl | Me | H | H | H | Et |
| bA609 | bB609 | $OCH_2$ | p-MeO-Bzl | Me | OMe | H | H | H |
| bA610 | bB610 | $OCH_2$ | p-MeO-Bzl | Me | H | OMe | H | H |
| bA611 | bB611 | $OCH_2$ | p-MeO-Bzl | Me | H | H | OMe | H |
| bA612 | bB612 | $OCH_2$ | p-MeO-Bzl | Me | H | H | H | OMe |
| bA613 | bB613 | $OCH_2$ | p-MeO-Bzl | Me | F | H | H | H |
| bA614 | bB614 | $OCH_2$ | p-MeO-Bzl | Me | H | F | H | H |
| bA615 | bB615 | $OCH_2$ | p-MeO-Bzl | Me | H | H | F | H |
| bA616 | bB616 | $OCH_2$ | p-MeO-Bzl | Me | H | H | H | F |
| bA617 | bB617 | $OCH_2$ | i-Pr | Me | Me | H | H | F |
| bA618 | bB618 | $OCH_2$ | i-Pr | Me | H | Me | H | H |
| bA619 | bB619 | $OCH_2$ | i-Pr | Me | H | H | Me | H |
| bA620 | bB620 | $OCH_2$ | i-Pr | Me | H | H | H | Me |
| bA621 | bB621 | $OCH_2$ | i-Pr | Me | Cl | H | H | H |
| bA622 | bB622 | $OCH_2$ | i-Pr | Me | H | Cl | H | H |
| bA623 | bB623 | $OCH_2$ | i-Pr | Me | H | H | Cl | H |
| bA624 | bB624 | $OCH_2$ | i-Pr | Me | H | H | H | Cl |
| bA625 | bB625 | $OCH_2$ | i-Pr | Me | Et | H | H | H |
| bA626 | bB626 | $OCH_2$ | i-Pr | Me | H | Et | H | H |

TABLE 2-continued

Compounds of the formula (Ib-A) and (Ib-B)

(Ib-A)

(Ib-B)

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA627 | bB627 | $OCH_2$ | i-Pr | Me | H | H | Et | H |
| bA628 | bB628 | $OCH_2$ | i-Pr | Me | H | H | H | Et |
| bA629 | bB629 | $OCH_2$ | i-Pr | Me | OMe | H | H | H |
| bA630 | bB630 | $OCH_2$ | i-Pr | Me | H | OMe | H | H |
| bA631 | bB631 | $OCH_2$ | i-Pr | Me | H | H | OMe | H |
| bA632 | bB632 | $OCH_2$ | i-Pr | Me | H | H | H | OMe |
| bA633 | bB633 | $OCH_2$ | i-Pr | Me | F | H | H | H |
| bA634 | bB634 | $OCH_2$ | i-Pr | Me | H | F | H | H |
| bA635 | bB635 | $OCH_2$ | i-Pr | Me | H | H | F | H |
| bA636 | bB636 | $OCH_2$ | i-Pr | Me | H | H | H | F |
| bA637 | bB637 | $OCH_2$ | t-Bu | Me | H | H | H | H |
| bA638 | bB638 | $OCH_2$ | t-Bu | Me | Me | H | H | H |
| bA639 | bB639 | $OCH_2$ | t-Bu | Me | Me | Me | H | H |
| bA640 | bB640 | $OCH_2$ | t-Bu | Me | H | H | Me | H |
| bA641 | bB641 | $OCH_2$ | t-Bu | Me | H | H | H | Me |
| bA642 | bB642 | $OCH_2$ | t-Bu | Me | Cl | H | H | H |
| bA643 | bB643 | $OCH_2$ | t-Bu | Me | H | Cl | H | H |
| bA644 | bB644 | $OCH_2$ | t-Bu | Me | H | H | Cl | H |
| bA645 | bB645 | $OCH_2$ | t-Bu | Me | H | H | H | Cl |
| bA646 | bB646 | $OCH_2$ | t-Bu | Me | H | H | H | H |
| bA647 | bB647 | $OCH_2$ | t-Bu | Me | Et | H | H | H |
| bA648 | bB648 | $OCH_2$ | t-Bu | Me | H | Et | H | H |
| bA649 | bB649 | $OCH_2$ | t-Bu | Me | H | H | Et | H |
| bA650 | bB650 | $OCH_2$ | t-Bu | Me | H | H | H | Et |
| bA651 | bB651 | $OCH_2$ | t-Bu | Me | OMe | H | H | H |
| bA652 | bB652 | $OCH_2$ | t-Bu | Me | H | OMe | H | H |
| bA653 | bB653 | $OCH_2$ | t-Bu | Me | H | H | OMe | H |
| bA654 | bB654 | $OCH_2$ | t-Bu | Me | H | H | H | OMe |
| bA655 | bB655 | $OCH_2$ | t-Bu | Me | F | H | H | H |
| bA656 | bB656 | $OCH_2$ | t-Bu | Me | H | F | H | H |
| bA657 | bB657 | $OCH_2$ | t-Bu | Me | H | H | F | H |
| bA658 | bB658 | $OCH_2$ | t-Bu | Me | H | H | H | F |
| bA659 | bB659 | $OCH_2$ | Ph | Me | H | H | H | H |
| bA660 | bB660 | $OCH_2$ | Ph | Me | Me | H | H | H |
| bA661 | bB661 | $OCH_2$ | Ph | Me | Me | Me | H | H |
| bA662 | bB662 | $OCH_2$ | Ph | Me | H | H | Me | H |
| bA663 | bB663 | $OCH_2$ | Ph | Me | H | H | H | Me |
| bA664 | bB664 | $OCH_2$ | Ph | Me | Cl | H | H | H |
| bA665 | bB665 | $OCH_2$ | Ph | Me | H | Cl | H | H |
| bA666 | bB666 | $OCH_2$ | Ph | Me | H | H | Cl | H |
| bA667 | bB667 | $OCH_2$ | Ph | Me | H | H | H | Cl |
| bA668 | bB668 | $OCH_2$ | Ph | Me | H | H | H | H |
| bA669 | bB669 | $OCH_2$ | Ph | Me | Et | H | H | H |
| bA670 | bB670 | $OCH_2$ | Ph | Me | H | Et | H | H |
| bA671 | bB671 | $OCH_2$ | Ph | Me | H | H | Et | H |
| bA672 | bB672 | $OCH_2$ | Ph | Me | H | H | H | Et |
| bA673 | bB673 | $OCH_2$ | Ph | Me | OMe | H | H | H |
| bA674 | bB674 | $OCH_2$ | Ph | Me | H | OMe | H | H |

TABLE 2-continued

Compounds of the formula (Ib-A) and (Ib-B)

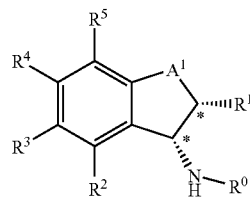
(Ib-A)

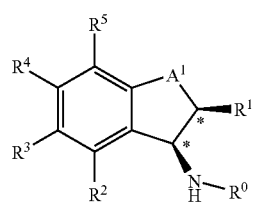
(Ib-B)

The numbers in the first column of the table relate to the compounds of the formula (Ib-A) with the substituent definitions in the columns under A, $R^0$ to $R^5$. Correspondingly, the numbers in the second column relate to the compounds of the formula (Ib-B) with the substituent definitions in the columns under A and $R^0$ to $R^5$.

| Ib-A | Ib-B | $A^1$ | $R^0$ | $R^1$ | $R^2$ | $R^3$ | $R^4$ | $R^5$ |
|---|---|---|---|---|---|---|---|---|
| bA675 | bB675 | $OCH_2$ | Ph | Me | H | H | OMe | H |
| bA676 | bB676 | $OCH_2$ | Ph | Me | H | H | H | OMe |
| bA677 | bB677 | $OCH_2$ | Ph | Me | F | H | H | H |
| bA678 | bB678 | $OCH_2$ | Ph | Me | H | F | H | H |
| bA679 | bB679 | $OCH_2$ | Ph | Me | H | H | F | H |
| bA680 | bB680 | $OCH_2$ | Ph | Me | H | H | H | F |

Physical data on compounds from table 2:
Compound No.: bA214: Ref($^1$), $R_t$ = 6.7, n-hexane/isopropanol = 92:8 (v/v), flow rate = 0.5 ml/min,
Compound No.: bA218: Ref($^{1,4}$), $R_t$ = 13.9, n-hexane/isopropanol = 90:10 (v/v), Flow rate = 1.0 ml/min,
Compound No.: bA237: Ref($^3$), $R_t$ = 17.4, n-hexane/isopropanol = 99:1 (v/v), flow rate = 0.3 ml/min,
Compound No.: bB237: Ref($^3$), $R_t$ = 19.9, n-hexane/isopropanol = 99:1 (v/v), flow rate = 0.3 ml/min,
Compound No.: bA239: Ref($^{3,4}$), $R_t$ = 12.3, n-hexane/isopropanol = 90:10 (v/v), flow rate = 1.0 ml/min,
Compound No.: bA406: Ref($^1$), $R_t$ = 7.1, n-hexane/isopropanol = 96:4 (v/v), flow rate = 0.5 ml/min.

What is claimed is:

1. A process for preparing optically active cyclic amines of the formula (I) or salts thereof

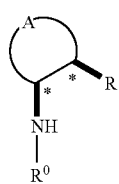
(I)

in which

A, together with the carbon atoms designated with an asterisk (*) in each case, is a carbocyclic or heterocyclic, saturated or unsaturated, nonaromatic ring which has from 3 to 30 ring atoms, and may be further substituted in addition to the $R^1$ and NH—$R^0$ radicals, $R^0$, independently of R, is a $(C_1-C_6)$alkyl, $(C_3-C_6)$alkenyl or $(C_3-C_1)$alkynyl radical, where each of the three latter radicals may be unsubstituted or substituted by one or more radicals selected from the group consisting of halogen, cyano, $(C_1-C_4)$alkoxy, $(C_1-C_4)$haloalkoxy, $(C_1-C_4)$alkylthio, $(C_1-C_4)$oyloxy, $(C_1-C_4)$haloalkanoyloxy, aryl, aryloxy, amyl, aroyloxy and heterocyclyl, where each of the latter 5 radicals is unsubstituted or substituted, or $(C_3-C_9)$cycloalkyl, $(C_4-C_9)$cycloalkenyl, aryl or heterocyclyl, where each of the latter 4 radicals is unsubstituted or substituted, R, independently of $R^0$, is $(C_1-C_6)$alkyl, $(C_2-C_6)$alkenyl or $(C_2-C_6)$alkynyl, where each of the three latter radicals is unsubstituted or substituted by one or more radicals selected from the group consisting of halogen, cyano, $(C_1-C_6)$alkoxy, $(C_1-C_6)$haloalkoxy, $(C_1-C_6)$alkylthio, aryl which is unsubstituted or substituted, and heteroaryl which is unsubstituted or substituted, or aryl which is unsubstituted or substituted, or heteroaryl which is unsubstituted or substituted, or $R^0$ and A form a ring B1 and, together with the NH group and the carbon atom which is designated with an asterisk (*) and is bonded to the NH group, are a heterocyclic ring which has from 4 to 30 ring atoms, and is optionally additionally further substituted and which optionally contains 1 or 2 further heteroatoms from the group of N, O and S, or R and A form a ring B2 and, together with the carbon atom which is designated with an asterisk (*) and is bonded to R, are a carbocyclic or heterocyclic ring which has from 3 to 30 ring atoms, and is optionally additionally further substituted, and which, in the case of a heterocyclic ring, contains 1, 2 or 3 further heteroatoms from the group of N, O and S, or $R^0$ and R form a ring B3 and, together with the NH group and the carbon atoms designated with an asterisk (*) in each case, are a heterocyclic ring which has from 4 to 30 ring atoms, and is optionally additionally further substituted and which optionally contains 1 or 2 further heteroatoms from the group of N, O and S, or $R^0$ and R and, if appropriate, A may simultaneously form two or more of the rings B1, B2 and B3 mentioned, where R and the NH—$R^0$ group on the two ring carbon atoms marked with an asterisk (*) in each case are arranged in cis arrangement to one another and the stereochemical configuration on these carbon atoms is different from the racemic configuration, which comprises converting an imine of the formula (II) or a salt thereof

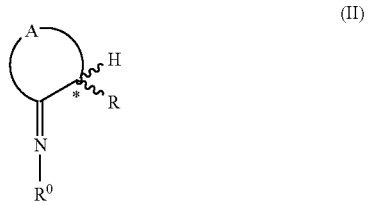

(II)

where A, $R^0$ and R are each as defined in formula (I) and the compound of the formula (II), with regard to the ring carbon atom marked with an asterisk (*), is present in the form of a racemic mixture or in the form of a mixture with any other isomeric ratio of the stereoisomers in question, in the presence of hydrogen or a hydrogen donor and a non-enzymatic catalyst which comprises a catalytically active optically active complex of one or more transition metals from the group of ruthenium, rhodium, palladium, iridium, osmium, platinum, iron, nickel and samarium, with organic ligands, to the compound of the formula (I).

2. The process as claimed in claim 1, wherein the compounds (I) or salts thereof with cis configuration on the two chiral centers designated with an asterisk (*) in each case are obtained with a selectivity of from 60 to 100% in comparison to the trans configuration, one enantiomer of the cis compound being obtained with an enantioselectivity of in each case more than 20% ee based on the total content of enantiomers of the cis compound.

3. The process as claimed in claim 1, wherein compounds of the formula (Ia) or salts thereof are prepared

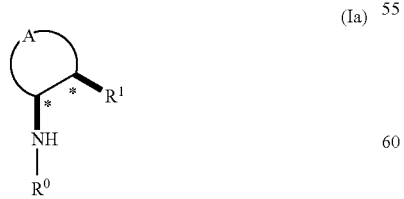

(Ia)

in which

A, together with the carbon atoms designated with an asterisk (*) in each case, is a carbocyclic or heterocyclic, saturated or unsaturated, nonaromatic ring having from 3 to 30 ring atoms and, in the case of a heterocyclic ring which has from 1 to 3 heterocyclic ring atoms from the group of N, O and S and, in addition to the $R^1$ and NH—$R^0$ radicals is unsubstituted or further substituted by one or more radicals selected from the group consisting of halogen, hydroxy, amino, cyano, nitro, $(C_1$-$C_4)$alkyl, $(C_3$-$C_9)$cycloalkyl, $(C_1$-$C_4)$alkoxy, $(C_1$-$C_4)$alkoxycarbonyl, $(C_1$-$C_4)$alkylthio, $(C_1$-$C_4)$alkylsulfonyl, aryl and heterocyclyl, where each of the latter 8 radicals is unsubstituted or substituted by one or more radicals selected from the group consisting of halogen, cyano, $(C_3$-$C_9)$cycloalkyl, $(C_1$-$C_4)$alkoxy, $(C_1$-$C_4)$alkylthio and, in the case of cyclic radicals, also $(C_1$-$C_4)$alkyl and $(C_1$-$C_4)$haloalkyl, $R^0$ independently of $R^1$, is a $(C_1$-$C_6)$alkyl, $(C_2$-$C_6)$alkenyl or $(C_3$-$C_6)$alkynyl radical, where each of the three latter radicals is unsubstituted or substituted by one or more radicals selected from the group consisting of halogen, cyano, $(C_1$-$C_4)$alkoxy, $(C_1$-$C_4)$haloalkoxy, $(C_1$-$C_4)$alkylthio, $(C_1$-$C_4)$alkanoyloxy, $(C_1$-$C_4)$haloalkanoyloxy, aryl, aryloxy, aroyl, aroyloxy and heterocyclyl, where each of the latter 5 radicals is unsubstituted or substituted, or $(C_3$-$C_9)$cycloalkyl, $(C_4$-$C_9)$cycloalkenyl, aryl or heterocyclyl, where each of the latter 4 radicals is unsubstituted or substituted, $R^1$, independently of $R^0$, is $(C_1$-$C_6)$alkyl, $(C_2$-$C_6)$alkenyl or $(C_2$-$C_6)$alkynyl, where each of the three latter radicals is unsubstituted or substituted by one or more radicals selected from the group consisting of halogen, cyano, $(C_1$-$C_4)$alkoxy, $(C_1$-$C_4)$haloalkoxy and $(C_1$-$C_4)$alkylthio, or aryl or heterocyclyl, where each of the 2 latter radicals is unsubstituted or substituted, where the substituents $R^1$ and the amino group on the two ring carbon atoms marked with an asterisk (*) in each case are arranged in cis arrangement to one another and the compound (Ia) is present in the form of a stereochemically pure compound of the formula (Ia-A) or (Ia-B)

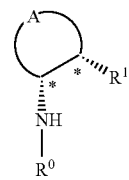

(Ia-A)

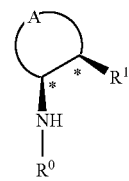

(Ia-B)

in which the general radicals are each as defined in formula (Ia), or in the form of an isomer mixture of the compounds of the formulae (Ia-A) and (Ia-B) in an isomer ratio other than the ratio of 1:1.

4. The process as claimed in claim 1, wherein compounds of the formula (Ib) or salts thereof are prepared

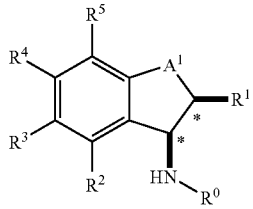
(Ib)

in which

A¹ is a direct bond or a group of the formula $(CR^6R^7)_n$ in which n is from 1 to 6 and $R^6$ and $R^7$ are each independently, or, in the case that n is greater than 1, the $R^6$ and $R^7$ radicals are in each case independently hydrogen, $(C_1-C_4)$alkyl, $(C_1-C_4)$haloalkyl, halogen, $(C_1-C_4)$alkoxy or $(C_1-C_4)$haloalkoxy, where individual $CR^6R^7$ groups may be replaced by heteroatoms from the group of O and S, $R^0$, independently of $R^1$, is a $(C_1-C_6)$alkyl or $(C_2-C_6)$alkenyl radical, where each of the two latter radicals is unsubstituted or substituted by one or more radicals selected from the group consisting of halogen, cyano, $(C_1-C_4)$alkoxy, $(C_1-C_4)$haloalkoxy, $(C_1-C_4)$alkylthio, $(C_1-C_4)$alkanoyloxy, $(C_1-C_4)$haloalkanoyloxy, aryl, aryloxy, aroyl, aroyloxy and heterocyclyl, where each of the latter 5 radicals is unsubstituted or substituted, or $(C_3-C_9)$cycloalkyl, $(C_4-C_9)$cycloalkenyl, aryl or heterocyclyl, where each of the latter 4 radicals is unsubstituted or substituted, $R^1$, independently of $R^0$, is $(C_1-C_6)$alkyl which is unsubstituted or substituted by one or more radicals selected from the group consisting of halogen, cyano, $(C_1-C_4)$alkoxy, $(C_1-C_4)$haloalkoxy, $(C_1-C_4)$allylthio and aryl which is optionally substituted, and heterocyclyl which is optionally substituted, or aryl which is optionally substituted, or heterocyclyl which is optionally substituted, and $R^2$ is H, $(C_1-C_4)$alkyl, $(C_1-C_3)$haloalkyl, halogen, $(C_1-C_3)$alkoxy, $(C_1-C_3)$haloalkoxy or CN, $R^3$ is H, $(C_1-C_4)$alkyl, $(C_1-C_3)$haloalkyl, halogen, $(C_1-C_3)$alkoxy, $(C_1-C_3)$haloalkoxy or CN, $R^4$ is H, $(C_1-C_4)$alkyl, $(C_1-C_3)$haloalkyl, halogen, $(C_1-C_3)$alkoxy, $(C_1-C_3)$haloalkoxy or CN and $R^5$ is H, $(C_1-C_4)$alkyl, $(C_1-C_3)$haloalkyl, halogen, $(C_1-C_3)$alkoxy, $(C_1-C_3)$haloalkoxy or CN, where the substituents $R^1$ and the amino group on the two ring carbon atoms marked with an asterisk (*) in each case are arranged in cis arrangement to one another and the compound is present in the form of a stereochemically pure compound of the formula (Ib-A) or (Ib-B)

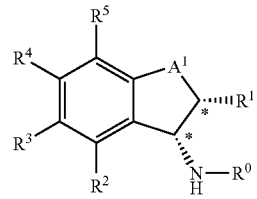
(Ib-A)

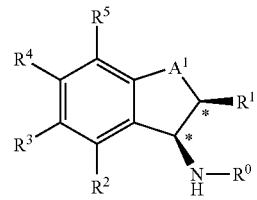
(Ib-B)

in which the general radicals are each as defined in formula (Ib), or in the form of an isomer mixture of the compounds of the formulae (Ib-A) and (Ib-B) in an isomer ratio other than the ratio of 1:1.

5. The process as claimed in claim 1, wherein the reaction is carried out in the presence of an inert organic solvent or in substance.

6. The process as claimed in claim 1, wherein the reaction is carried out as a catalytic hydrogenation.

7. The process as claimed in claim 1, wherein the reaction is carried out as a catalytic transfer hydrogenation.

8. The process as claimed in claim 7, wherein the reaction is carried out with formic acid as a hydrogen donor in the presence of a tertiary amine.

9. The process as claimed in claim 1, wherein the imine of the formula (II) is prepared in situ from the corresponding ketone and an amine of the formula and reduced.

10. The process as claimed in claim 2, wherein the compounds (I) or salts thereof with cis configuration on the two chiral centers designated with an asterisk (*) in each case are obtained with one enantiomer of the cis compound being obtained with an enantioselectivity of in each case more than 50% ee based on the total content of enantiomers of the cis compound.

* * * * *